US006925202B2

(12) United States Patent
Karklin et al.

(10) Patent No.: US 6,925,202 B2
(45) Date of Patent: Aug. 2, 2005

(54) SYSTEM AND METHOD OF PROVIDING MASK QUALITY CONTROL

(75) Inventors: Linard Karklin, Sunnyvale, CA (US); Linyong Pang, Stanford, CA (US); Lynn Cai, Union City, CA (US)

(73) Assignee: Synopsys, Inc., Mountain View, CA (US)

( * ) Notice: Subject to any disclaimer, the term of this patent is extended or adjusted under 35 U.S.C. 154(b) by 776 days.

(21) Appl. No.: 09/814,025

(22) Filed: Mar. 20, 2001

(65) Prior Publication Data

US 2002/0164064 A1 Nov. 7, 2002

(51) Int. Cl.[7] .............................................. G06K 9/00
(52) U.S. Cl. ..................... 382/145; 382/209; 348/126; 356/237.4
(58) Field of Search ................................. 382/100, 141, 382/143, 144, 145, 146, 147, 148, 149, 150, 151, 152, 162, 168, 169, 184, 209, 211, 213, 274, 275; 356/399, 237.4, 237.1, 400, 401; 348/87, 86, 125, 126, 127, 131; 703/13, 28; 700/58, 57, 212; 430/4, 5; 438/15, 16, 20, 29

(56) References Cited

U.S. PATENT DOCUMENTS

| | | | |
|---|---|---|---|
| 5,326,659 A | * 7/1994 | Liu et al. ........................ 430/5 |
| 5,340,700 A | 8/1994 | Chen et al. .................. 430/312 |
| 5,432,714 A | 7/1995 | Chung et al. ................ 364/525 |
| 5,572,598 A | * 11/1996 | Wihl et al. .................. 382/144 |
| 5,795,688 A | 8/1998 | Burdorf et al. ............... 430/30 |
| 5,801,954 A | 9/1998 | Le et al. ..................... 364/488 |
| 5,804,340 A | * 9/1998 | Garza et al. .................... 430/5 |
| 5,815,685 A | 9/1998 | Kamon ....................... 395/500 |
| 5,825,647 A | * 10/1998 | Tsudaka ....................... 700/57 |
| 5,849,440 A | 12/1998 | Lucas et al. .................... 430/5 |
| 5,862,058 A | 1/1999 | Samuels et al. ............. 364/491 |
| 5,900,338 A | 5/1999 | Garza et al. .................... 430/5 |
| 6,009,250 A | 12/1999 | Ho et al. ............... 395/500.06 |
| 6,009,251 A | 12/1999 | Ho et al. ............... 395/500.06 |
| 6,011,911 A | 1/2000 | Ho et al. ............... 395/500.06 |

(Continued)

FOREIGN PATENT DOCUMENTS

| WO | WO 97/13370 | 4/1997 |
|---|---|---|
| WO | WO 98/20327 | 5/1998 |

(Continued)

OTHER PUBLICATIONS

Lin, B.J., et al., "Single–Level Electric Testsites for Phase–Shifting Masks", SPIE, vol. 1673, pp. 221–228, Mar. 9–11, 1992.

(Continued)

Primary Examiner—Kanjibhai Patel
Assistant Examiner—Seyed Azarian
(74) Attorney, Agent, or Firm—Bever, Hoffman & Harms, LLP; Jeanette S. Harms

(57) ABSTRACT

A simulated wafer image of a physical mask and a defect-free reference image are used to generate a severity score for each defect, thereby giving a customer meaningful information to accurately assess the consequences of using a mask or repairing that mask. The defect severity score is calculated based on a number of factors relating to the changes in critical dimensions of the neighbor features to the defect. A common process window can also be used to provide objective information regarding defect printability. Certain other aspects of the mask relating to mask quality, such as line edge roughness and contact corner rounding, can also be quantified by using the simulated wafer image of the physical mask.

41 Claims, 26 Drawing Sheets

U.S. PATENT DOCUMENTS

| | | | | |
|---|---|---|---|---|
| 6,016,357 | A | * | 1/2000 | Neary et al. ................. 382/144 |
| 6,023,328 | A | * | 2/2000 | Pierrat ..................... 356/237.4 |
| 6,076,465 | A | | 6/2000 | Vacca et al. ................. 101/481 |
| 6,078,738 | A | | 6/2000 | Garza et al. ........... 395/500.22 |
| 6,081,659 | A | | 6/2000 | Garza et al. ........... 395/500.22 |
| 6,091,845 | A | | 7/2000 | Pierrat et al. ............... 382/144 |
| 6,130,750 | A | * | 10/2000 | Ausschnitt et al. ......... 356/401 |
| 6,171,731 | B1 | * | 1/2001 | Medvedeva et al. ............ 430/5 |
| 6,272,236 | B1 | | 8/2001 | Pierrat et al. ............... 382/144 |
| 6,334,209 | B1 | | 12/2001 | Hashimoto et al. ........... 716/21 |
| 6,346,426 | B1 | | 2/2002 | Toprac et al. .................. 438/8 |
| 6,556,703 | B1 | * | 4/2003 | Kane et al. ................. 382/145 |
| 6,647,147 | B1 | * | 11/2003 | Miyano ..................... 382/199 |
| 2002/0019729 | A1 | | 2/2002 | Chang et al. .................. 703/6 |
| 2002/0164064 | A1 | | 11/2002 | Karklin et al. .............. 382/145 |
| 2002/0164065 | A1 | | 11/2002 | Cai et al. .................... 382/149 |

FOREIGN PATENT DOCUMENTS

| | | |
|---|---|---|
| WO | WO 98/45685 | 10/1998 |
| WO | WO 99/14706 A2 | 3/1999 |
| WO | WO 99/14706 A3 | 3/1999 |
| WO | WO 99/38002 | 7/1999 |
| WO | WO 99/56113 | 11/1999 |
| WO | WO 99/59200 | 11/1999 |
| WO | WO 99/67626 | 12/1999 |
| WO | WO 00/36525 A3 | 6/2000 |
| WO | WO 00/67074 A1 | 11/2000 |
| WO | WO 00/67075 A1 | 11/2000 |
| WO | WO 00/67076 A1 | 11/2000 |

OTHER PUBLICATIONS

Spence, C., et al., "Detection of 60(degree) Phase Defects on Alternating PSMs", Advanced Micro Devices, KLA–Tencor, DuPont RTC (2 pages).

Ogawa, K., et al., "Phase Defect Inspection by Differential Interference", Lasertee Corporation (12 pages).

Socha, R., et al., "Printability of Phase–Shift Defects Using a Perturbational Model", Univ. of California Berkeley, Sematech (11 pages).

Fiekowsky, P., "The End of Thresholds: Subwavelength Optical Linewidth Measurement Using the Flux–Area Technique", Automated Visual Inspection (6 pages).

Watanbe, H., et al., "Detection and Printability of Shifter Defects in Phase–Shifiting Masks", Japanese Journal of Applied Physics, vol. 30, No. 11B, pp. 3016–3020, Nov. 1991.

Hosono, K., et al., "A Novel Architecture for High Speed Dual Image Generation of Pattern Data for Phase Shifting Reticle Inspection", SPIE—Integrated Circuit Metrology, Inspection, and Process Control VI, vol. 1673, pp. 229–236 (1992).

Ohtsuka, H., et al., "Evaluation of Repair Phase and Size Tolerance for a Phase–Shift Mask", J. Vac. Sci. Technol. B, vol. 11, No. 6, pp. 2665–2668, Nov./Dec. 1993.

Reynolds, J., "Elusive Mask Defects: Reflectivity Variations", Solid State Technology, pp. 75–76, Mar. 1995.

Kusunose, H., et al., "Direct Phase–Shift Measurement with Transmitted Deep–UV Illumination", SPIE. vol. 2793, pp. 251–260 (1996).

Fiekowsky, P., et al., "Direct Printability Measurement on the KLA–351: Correlation to Defect Sizing Using the AVI Metrology System", SPIE 19th Annual BACUS Symposium on Photomask Technology and Management Conference, pp. 1–6, Sep. 1999.

Tejnil, E., et al., "Option for At–Wavelegnth Inspection of Patterned Extreme Ultraviolet Lithography Masks", SPIE Bacus '99, pp. 1–12 (1999).

Hemar, S., et al., "Finding Killer CD Variations by Full–Reticle CD Mapping", Microlithography World, pp. 4, 6, 8 & 10 (Summer 2000).

Adam, K., et al., "Simplified Models for Edge Transitons in Rigorous Mask Modeling", University of California Berkeley (40 pages).

Gordon, R., et al., "Mask Topography Simulation for EUV Lithography", FINLE Technologies Inc. (15 pages).

Pistor, T., "Rigorous 3D Simulation of Phase Defects in Alternating Phase–Shifting Masks", Panoramic Technology Inc. (13 pages).

Semmier, A., et al., "Application of 3D EMF Simulation for Development and Optimization of Alternating Phase Shifiting Masks", Infineon Technologies AG (12 pages).

Wong, A., et al., "Polarization Effects in Mask Transmission", University of California Berkeley (8 pages).

Neureuther, A., et al., "Modeling Defect–Feature Interactions in the Presence of Aberrations", University of California Berkeley (10 pages).

Mathur, B.P., et al., "Quantitative Evaluation of Shape of Image on Photoresist of Square Apertures", IEEE, Transactions On Electron Devices, vol. 35, No. 3, pp. 294–297, Mar. 1988.

Crisalle, O., et al., "A Comparison of the Optical Projection Lithography Simulators in SAMPLE and PROLITH", IEEE, Transactions On Semiconductors Manufacturing, vol. 5, No. 1, pp. 14–26, Feb. 1992.

Qian, Q.D., et al., "A New Scalar Planeawave Model for High NA Lithography Simulators", IEEE, pp. 45–48 (1994).

Balasinski, A., et al., "A Novel Approach to Simulate the Effect of Optical Proximity on MOSFET Parametric Yield", IEEE, pp. 37.6.1–37.6.4 (1999).

Balasinski, A., et al., "Comparison of Mask Writing Tools and Mask Simulations for 0.16um Devices", IEEE, SEMI Advanced Semiconductor Manufacturing Conference, pp. 372–377 (1999).

Brunner, T. et al., "Approximate Models For Resist Effects", SPIE, vol. 2726, pp. 198–207, Mar. 1996.

Casey, Jr., J.D. et al., "Chemically Enhanced FIB Repair Of Opaque Defects On Molybdenum Silicide Photomasks", SPIE, vol. 3236, pp. 487–497 (1997).

Chang, K. et al., "Accurate Modeling of Deep Submicron Interconnect Technology", TMA Times, vol. IX, No. 3, (1997).

Cobb, et al., "Fast Sparse Aerial Image Calculation For OPC", SPIE, vol. 2621 534–544.

Fukuda, H. et al., "Determination Of High–Order Lens Aberration Using Phase/Amplitude Linear Algebra", J. Vac. Sci. Technol. B, vol. 17, No. 6, pp. 3318–3321, Nov./Dec. 1999.

Fukuda, H., "Node–Connection/Quantum Phase–Shifting Mask: Path to Below 0.3 $\mu$m Pitch, Proximity Effect Free, Random Interconnects And Memory Patterning", J. Vac. Sci. Technol. B, vol. 17, No. 6, pp. 3291–3295, Nov./Dec. 1999.

Gans, F. et al., "Printability And Repair Techniques For DUV Photomasks", SPIE, Proceedings of the 17$^{th}$ Annual Symposium on Photomask Technology and Management, vol. 3236, pp. 136–141 (1997).

Ham, Y.M. et al., "Dependence Of Defects In Optical Lithography", Jpn. J. Appl. Phys., vol. 31, pp. 4137–4142 (1992).

Henke, W. et al., "A Study Of Reticle Defects Imaged Into Three–Dimensional Developed Profiles Of Positive Photoresist Using The Solid Lithography Simulator", *Microelectronics Eng.*, vol. 14, pp. 283–297 (1991).

Ibsen, K. et al., "Clear Field Reticle Defect Disposition For Advanced Sub–Half Micron Lithography", *SPIE*, Proceedings of the 17th Annual Symposium on Photomask Technology and Management, vol. 3236, pp. 124–135 (1997).

Karklin, L., "A Comprehensive Simulation Study Of The Photomask Defects Printability", *SPIE*, vol. 2621, pp. 490–504 (1995).

Kubota, H. et al., "A Fast Method Of Simulating Resist Pattern Contours Based On Mean Inhibitor Concentration", *Jpn. J. Appl. Phys.*, vol. 37, pp. 5815–5820 (1998).

Neureuther, A., "Modeling Phase Shifting Masks", *SPIE*, 10th Annual Symposium on Microlithography, vol. 1496, pp. 80–85 (1990).

Nistler, J. et al., "Large Area Optical Design Rule Checker For Logic PSM Application", *SPIE*, Photomask and X–Ray Mask Technology, vol. 2254, pp. 78–92 (1994).

Nistler, J. et al., "Phase Shift Mask Defect Printability Analysis", Proceedings of the Microlithography Seminar INTERFACE '93, OCG Microelectronic Materials, Inc., pp. 11–28 (1993).

Ohtsuka, H. et al., "Phase Defect Repair Method For Alternating Phase Shift Masks Conjugate Twin–Shifter Method", *Jpn. J. Appl. Phys.*, vol. 31, pp. 4143–4149 (1992).

Pati, Y.C. et al., "Exploiting Structure In Fast Aerial Image Computation For Integrated Circuit Patterns", *IEEE Transactions on Semiconductor Manufacturing*, vol. 10, No. 1, pp. 62–74, Feb. 1997.

Pati, Y.C., et al., "Phase Shifting Masks for Microlithography: Automated Design And Mask Requirements", *J. Opt. Soc. Am.*, vol. 11, No. 9, pp. 2438–2452, Sep. 1994.

Rieger, M. et al., "System For Lithography Proximity Compensation", Precim Company, Portland, Oregon, Sep. 1993 (28 pages).

Spence, C. et al., "Automated Determination Of CAD Layout Failures Through Focus: Experiment And Simulation", *SPIE*, vol. 2197, pp. 302–313 (1994).

Stirniman, J. et al., "Spatial Filter Models to Describe IC Lithographic Behavior", Precim Corporation, Portland, Oregon (10 pages).

Sugawara, M. et al., "Defect Printability Study Of Attenuated Phase–Shifting Masks For Specifying Inspection Sensitivity", Semiconductor Company, Sony Corporation, Kanagawa, Japan (16 pages).

Vacca, A. et al., "100nm Defect Detection Using a Dynamically Programmable Image Processing Algorithm", *SPIE*, vol. 3236 (1997)(Abstract Only).

Vacca, A. et al., "100nm Defect Detection Using An Exisiting Image Acquisition System", *SPIE*, vol. 3236, pp. 208–214 (1998).

Watanabe, H. et al., "Detection And Printability Of Shifter Defects In Phase–Shifting Masks II Defocus Characteristics", *Jpn. J. Appl. Phys.*, vol. 31, pp. 4155–4160 (1992).

Wiley, J. et al., "Device Yield And Reliability By Specification Of Mask Defects", *Solid State Technology*, vol. 36, No. 7, pp. 65–66, 70, 72, 74, 77, Jul. 1993.

Wiley, J. et al., "The Effect Of Off–Axis Illumination On The Printability Of Opaque And Transparent Reticle Defects", *SPIE*, vol. 2512, pp. 432–440 (1995).

Wiley, J. et al., "Phase Shift Mask Pattern Accuracy Requirements And Inspection Technology", *SPIE*, Integrated Circuit Metrology, Inspection, and Process Control V, vol. 1464, pp. 346–355 (1991).

* cited by examiner

Figure 10A(2)
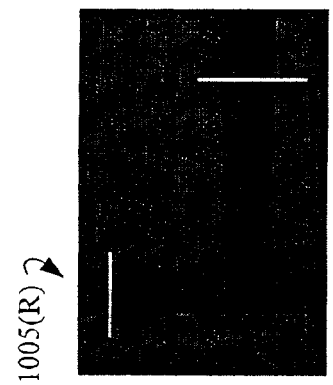
Figure 10B(2)
Figure 10A(2)
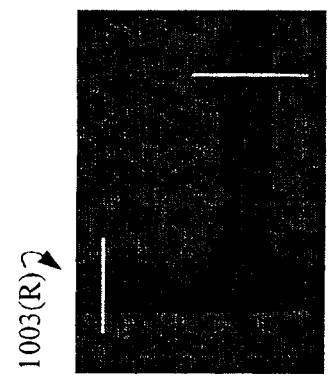
Figure 10B(2)
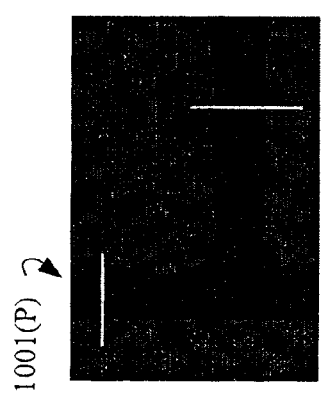
Figure 10A(1)
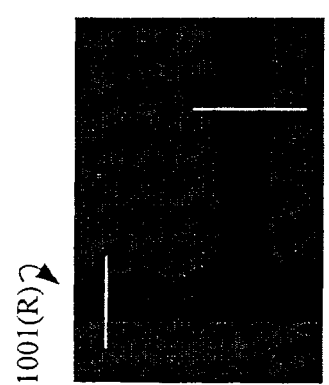
Figure 10B(1)

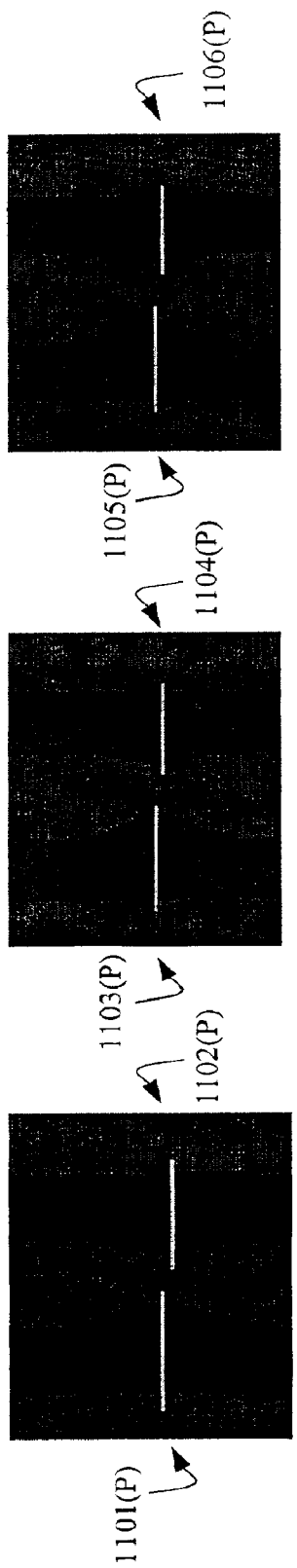
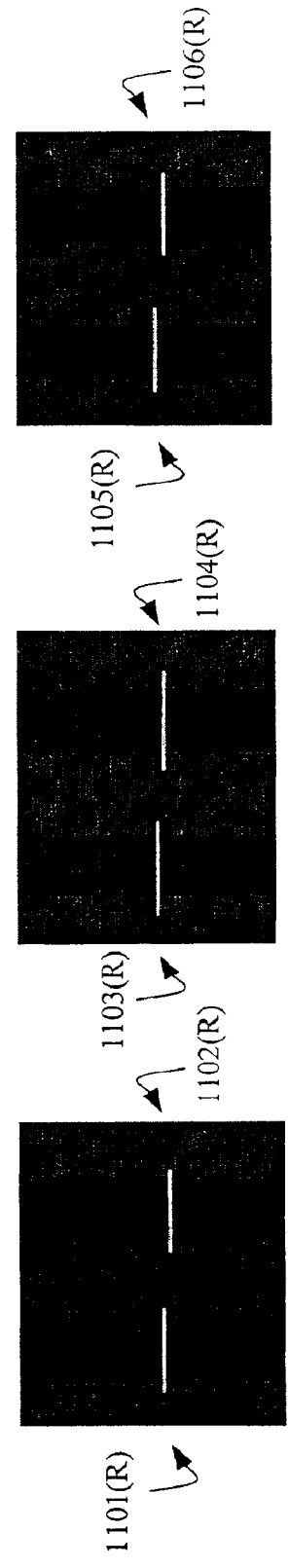
Figure 11A(1)  Figure 11A(2)  Figure 11A(3)
Figure 11B(1)  Figure 11B(2)  Figure 11(3)

SYSTEM AND METHOD OF PROVIDING MASK QUALITY CONTROL

FIELD OF THE INVENTION

An inspection of an integrated circuit mask including assessing mask quality is described.

BACKGROUND OF THE INVENTION

Mask/Reticle Defects

To fabricate an integrated circuit (IC) in a semiconductor substrate, a physical representation of the IC is transferred onto a pattern tool. Then, the pattern tool is exposed to transfer this pattern onto the semiconductor substrate. A mask is a standard pattern tool used in IC processing. Typically, a mask includes patterns that can be transferred to the entire semiconductor substrate (for example, a wafer) in a single exposure. A reticle, another standard pattern tool, must be stepped and repeated to expose the entire substrate surface. For ease of reference herein, the term "mask" refers to either a reticle or a mask.

A typical mask is formed from a quartz plate having a chrome coating. Generally, a mask is created for each layer of the IC design. Specifically, a portion of the IC layout data file representing a physical layer (such as a polysilicon layer or a metal layer) is etched into the chrome layer. Thus, each mask includes the pattern that represents the desired circuit layout for its corresponding layer. In high density ICs, a mask can also include optical proximity correction (OPC) features, such as serifs, hammerheads, bias, and assist bars. These OPC features are sub-resolution features used to compensate for process artifacts and/or proximity effects.

In high-density IC designs, those skilled in the art of IC fabrication have recognized the importance of using masks that provide accurate representations of the original design layout. Unfortunately, a "perfect" mask is not commercially viable. In fact, even under optimal manufacturing conditions, some mask defects can occur outside the controlled process.

A defect on a mask is any deviation from the design database (i.e. an irregularity) that is deemed unacceptable by an inspection tool or an inspection engineer. FIG. 1 illustrates a flowchart 100 of a prior art method of inspecting an integrated circuit. In step 110, an IC is designed. In step 112, a data file of mask design data, e.g. a layout of the IC, is created. This data is used to manufacture the mask in step 114. At this point, the mask is inspected in step 116 by scanning the surface of the mask with a high-resolution microscope and capturing images of the mask. Irregularities in the mask are identified in a list by their location. In one embodiment, the mask has an associated grid pattern and the list designates the squares in the grid pattern in which the irregularities are located. This inspection and irregularity identification can be performed by specialized equipment/software provided by companies such as KLA-Tencor or Applied Materials.

To determine whether the mask passes inspection (step 118), a skilled inspection engineer or a semi-automated inspection device reviews the irregularities identified in step 116. Note that only irregularities deemed to be outside the tolerance set by the manufacturer or user are characterized as defects. If irregularities are discovered and are outside tolerances, then a determination is made in step 128 if the mask can be repaired. If the mask can be repaired, then the mask is cleaned and/or repaired in step 130 and the process returns to step 116 of inspecting the mask. If the mask cannot be repaired, then a new mask must be manufactured and the inspection process returns to step 114. If the mask passes inspection, as determined in step 118, then an actual wafer is exposed using the mask in step 120.

To ensure that the mask has produced the desired image on the wafer, the wafer itself is typically inspected in step 122. If irregularities are discovered and are outside tolerances as determined in inspection step 124, then a determination is made in step 128 if the mask can be repaired. If the mask can be repaired, then the mask is cleaned and/or repaired in step 130 and the process returns to step 116 of inspecting the mask. If the mask cannot be repaired, then a new mask must be manufactured and the inspection process returns to step 114. If irregularities on the wafer are discovered, but are determined to be within tolerances, then the mask passes inspection in step 124 and the inspection process ends in step 126.

Unfortunately, the above-described process has a number of significant disadvantages. For example, an automated inspection device measures tolerance principally by size. Thus, if a pinhole on the mask has a predetermined size, then the automated inspection device would probably designate the pinhole as a defect regardless of its location on the mask. In contrast, a skilled inspection engineer can use additional, more subjective methods based on his/her level of experience. Specifically, an experienced engineer might be able to determine whether a pinhole of even less than the predetermined size but in a critical area would have an adverse effect on functionality or performance and therefore should be characterized a defect, or whether a pinhole greater than the predetermined size but not in a critical area would not affect functionality or performance. However, this skill set must be developed over time at considerable expense. Moreover, like all human activity, even after developing this skill set, the quality of review inevitably varies. Thus, the step of characterizing the irregularity is prone to error.

Another disadvantage of the above-described process is the triggering of false defect detections. For example, an automated inspection device can falsely report an OPC or an imperfect OPC feature as a defect. As noted previously, an OPC feature is a sub-resolution feature used to compensate for proximity effects. Therefore, the OPC feature would typically not constitute nor contribute to a defect.

Mask Inspection System

To address these disadvantages, a mask inspection system designed by Numerical Technologies, Inc. provides mask quality assessment without resorting to an actual exposure of a wafer. This mask inspection system is described in U.S. patent application Ser. No. 09/130,996 (herein referenced as the NTI system), entitled, "Visual Inspection and Verification System", which was filed on Aug. 7, 1998 and is incorporated by reference herein.

FIG. 2 illustrates a process 200 of inspecting a mask for defects in accordance with the NTI system. Process 200 utilizes an inspection tool 202 and a wafer image generator 209. In one embodiment, inspection tool 202 includes an image acquirer 203, typically a high resolution imaging device, to scan all or a portion of a physical mask 201. A defect detection processor 204 compares the mask images provided by image acquirer 203 to a set of potential defect criteria and determines what areas of the mask contain potential defects. If a potential defect is identified, defect detection processor 204 signals a defect area image generator 205 to provide a defect area image of the area including and surrounding the potential defect.

In one embodiment, inspection tool 202 then provides defect area image data 206 to wafer image generator 209. In another embodiment, this data is digitized by digitizing device 207, stored in storage device 208, and then provided to wafer image generator 209 at a later point in time. In yet another embodiment that analyzes both areas identified as potential defects and areas not identified as potential defects, the scanned image provided by image acquirer 203 can be provided directly to wafer image generator 209 or indirectly through digitizing device 207 and storage device 208.

Wafer image generator 209 includes an input device 210 that receives data directly from inspection tool 202 in a real time feed or off-line data from storage device 208. An image simulator 211 receives the information from input device 210 as well as other input data, such as lithography conditions 212. Lithography conditions 212 can include, but are not limited to, the wavelength of illumination, the numerical aperture, the coherence value, the defocus (wherein the term defocus as used herein refers to focal plane positioning), the exposure level, lens aberrations, substrate conditions, and the required critical dimension. Using these inputs, image simulator 211 can generate a wafer image 213 that simulates physical mask 201 being exposed on a wafer. Image simulator 211 can also generate a simulated process window 214, and performance output 215. In one embodiment, image simulator 211 also takes into account the photoresist and/or the etching process as indicated by block 216.

Although process 200 provides valuable information to the customer via the simulated wafer image 213, for example, the customer must still review that information to make a determination regarding the appropriate action to take (e.g. repair the mask or fabricate a new mask). Thus, process 200 can be subject to human error. Therefore, a need arises for a mask inspection system and process that provides an objective, accurate measure of mask defect printability and mask quality.

SUMMARY OF THE INVENTION

A system and method for analyzing defect printability is provided. In this analysis, a physical mask and a corresponding, defect-free reference image are inspected. In one embodiment, the defect-free reference image can be one of the following: a simulated image of the layout of the physical mask, a defect-free area of the physical mask having the same pattern, or a simulated image of the physical mask as it is processed in manufacturing.

This inspection identifies any defects, i.e. irregularities, of the physical mask compared to the reference image. If a defect is identified, a defect area image of the defect and the area surrounding the defect from the physical mask as well as the corresponding area image from the reference image are provided to a wafer image generator. The wafer image generator generates simulations of the image data, i.e. for the physical mask and reference image.

In one embodiment, the wafer image generator can receive a plurality of lithography conditions. These conditions include data that is specific to the lithography conditions and system parameters under which the physical mask will be exposed by the customer. Such data could include, for example, the wavelength of the illumination being used in the system (λ), the numerical aperture of the system (NA), the coherency value of the system (σ), the illumination type (e.g. off-axis or annular), the defocus, the exposure level, the lens aberrations, the substrate conditions, and the critical dimension (CD) of the design. In one embodiment, each parameter could include a range of values, thereby allowing the wafer image generator to generate a plurality of simulations based on a range of possible lithography conditions in different combinations.

Sub-wavelength production flow, which is highly non-linear, can be compensated for in the following manner. Specifically, to enhance the accuracy of the wafer images in sub-wavelength technology, the wafer image generator can also receive one or more conversion factors. The conversion factor can vary based on features on the mask, such as isolated lines, densely packed lines, and contacts. The conversion factor can also vary based on certain aspects of the fabrication process, including the stepper parameters and the photoresist.

In one embodiment, a test pattern provided on a test mask is simulated using the wafer image generator. The test pattern could include isolated lines of varying widths, densely pack lines of varying widths, and contacts of various sizes. Defect analysis, including any changes in critical dimension (CD), can be noted for each test pattern on the simulated wafer image. Note that as used herein, the CD is a measurement or calculated size of a specified location, which can be one-dimensional or two-dimensional. From this information, the conversion factor for each feature can be accurately calculated. Moreover, any number of simulations can be provided using various processes (e.g. lithography conditions) to obtain the conversion factors for these fabrication processes. A mask shop specific bias can also be included in the lithography conditions, thereby further enhancing the accuracy of the conversion factors generated by this embodiment.

This method of providing conversion factors is extremely cost-effective because it eliminates the cost associated with the printed wafer as well as the time for fabrication of that wafer. Moreover, because of the simulation environment, this method provides significant flexibility in optimizing system parameters before actual fabrication.

In accordance with one embodiment, a defect printability analysis generator receives the simulated wafer images of the physical mask and the reference image from the wafer image generator. In one embodiment, the two simulated wafer images are aligned in a pre-processing operation. Alignment can be done using defect free patterns in the mask or using coordinates from the masks. When these patterns or coordinates are aligned, the features provided on those masks (as well as on wafer images of those masks) are also aligned.

After alignment, two-dimensional analysis can proceed. In two-dimensional analysis, a defect on the simulated wafer image of the physical mask and the corresponding area on the simulated wafer image of the reference mask are identified. Then, any feature proximate to the defect (a neighbor feature) on the simulated wafer image of the physical mask is identified. In one simple implementation, any feature within a predetermined distance of the defect can be identified as a neighbor feature. In another embodiment, both the size of the defect and the distance of the defect from the neighbor feature are compared to measurements in a design rule table. The design rule table can identify, for each defect size (or range of sizes), a maximum distance from the defect, wherein if the feature is located less than the maximum distance from the defect, then the feature is a neighbor feature. Finally, any identified neighbor features are located on the simulated wafer image of the reference mask.

At this point, defect analysis on the simulated wafer images can be done. Defect analysis includes determining an average CD deviation (ACD), a relative CD deviation (RCD), and a maximum CD deviation (MCD). To calculate the ACD, a CD of a defect-free feature on the simulated wafer image of the physical mask is subtracted from the CD of the corresponding feature on the simulated wafer image of the reference mask. This difference is then divided by the CD of the corresponding feature on the simulated wafer image of the reference mask. This calculation generates a CD deviation of the simulated wafer physical image from the simulated wafer reference image (i.e. a calibration factor used for later calculations). For greater accuracy, more than one defect-free area can be analyzed to provide the ACD for defect-free areas. In one embodiment, ACDs are calculated for each exposure.

To calculate the relative CD deviation (RCD), a CD of an identified neighbor feature on the simulated wafer image of the reference mask is subtracted from the CD of the corresponding feature on the simulated wafer image of the physical mask. Note that a feature can be one-dimensional, such as a line or space, or two-dimensional, such as a contact hole, pile, post, serif, or some other area-based structure. This difference is then divided by the CD of the corresponding feature on the simulated wafer image of the reference mask. In one embodiment, the RCD can be calculated for each neighbor feature and for each exposure. The maximum CD deviation (MCD) among the RCDs can then be determined for each exposure level.

In accordance with one embodiment, the defect printability analysis generator can also receive information from a critical region identification generator. The critical region identification generator provides the defect printability analysis generator with information identifying areas of each mask that are designated critical regions, such as gates, that require a high degree of precision to ensure proper performance in the final IC device. This information is referred to as the tolerance for CD deviations (TCD). A defect in a critical region typically has a lower TCD than a defect in a non-critical region.

In accordance with one feature, a defect severity score (DSS) can be calculated using the average CD deviations (ACD), the maximum CD deviations (MCDs), the tolerance for CD deviations (TCD), and a variable N indicating the total number of exposures used. One exemplary equation for calculating this defect severity score is:

$$DSS = (3/N) \times \sum_{1}^{N} (MCD_i - (ACD_i/3))/TCD$$

In one embodiment, the defect printability analysis generator outputs a DSS having a scale from 1 to 10 in an impact report. This impact report can be used to reduce human error in defect printability analysis. For example, perhaps a predetermined DSS score could indicate that the printed features (as simulated by the inspection system) would have significant performance issues, but that repair of the physical mask is possible. On the other hand, perhaps a higher DSS score than above could indicate not only performance issues, but that re-fabrication of the physical mask is recommended. Thus, by providing a numerical result having an associated meaning for each number, a technician can proceed efficiently and without error to the next action, e.g. repair of the physical mask or re-fabrication of the physical mask.

In another feature, defect printability can also be objectively assessed using various process windows. Illustrative process windows are those provided by plots of defocus versus exposure deviation or depth of focus versus exposure latitude. Curves on these plots represent areas including a defect as well as defect-free areas. The largest rectangle fitting within these curves is termed the exposure defocus window, wherein a common process window is the intersection of multiple exposure defocus windows. Focus and exposure values that fall within the common process window produce resist features, e.g. CDs, within tolerance, whereas focus and exposure values that fall outside the process window produce resist features outside tolerance. Thus, analyzing the process windows associated with a feature can provide an objective means of determining the printability of that feature based on the proximity of a defect. In one embodiment, the defect printability analysis generator could determine a common process window for the features provided in physical and reference masks and provide this information in the impact report.

The impact report can be advantageously used to analyze repairs that could be done on a physical mask. Specifically, using the impact report (or portions therein), a bitmap editor can indicate possible corrections to be made to the physical mask to eliminate or significantly minimize the effects of one or more defects. The bitmap editor can then output a simulated mask including these corrections (the repaired mask).

Then, the repaired mask can be inspected by the inspection tool and used by the wafer image generator to generate a new, simulated wafer image and a new impact report that indicates the success of the possible corrections provided in the repaired mask. If the corrections are acceptable, then the bitmap editor can provide the correction information directly to the mask repair tools for repair of the physical mask. If the customer desires additional optimization or analysis of different parameters, then the above-described processes can be repeated until either the corrections are deemed to be within an acceptable range or the bitmap editor indicates that the desired result cannot be attained by repairing the physical mask.

In one embodiment, the bitmap editor can also indicate the optimized mask writing strategy, e.g. identify certain tools to be used for certain defects. Additionally, bitmap editor can receive inputs that indicate customer time or cost limitations, thereby allowing the bitmap editor to optimize the repair process based on these customer parameters. In yet another embodiment of the invention, the bitmap editor can be used to provide information to wafer repair tools. Specifically, the bitmap editor can include a program that compares the efficacy of repairing a mask versus repairing a wafer.

The defect printability analysis can be done on individual defects or on a plurality of defects. In one embodiment, the inspection tool and the wafer image generator can automatically provide outputs regarding all defects found on the physical mask. Thus, the resulting impact report could include defect severity scores on all defects.

Alternatively, if desired, the impact report could include only defect severity scores above a certain value. This tailored impact report could, in turn, be provided to the bitmap editor and subsequently to the mask repair tools. Therefore, the inspection system could encompass a complete, automated defect detection and correction process, thereby significantly reducing the time for a mask to be analyzed and repaired (if appropriate).

The defect printability analysis also eliminates the necessity of evaluating OPC features separately from other features. If an OPC feature prints (as determined by simulated wafer image) due to a defect, then the defect defect analysis can indicate this error as CD changes are determined. Thus, by eliminating any complicated design rules regarding OPC features, the inspection system ensures a quick, reliable, and accurate method to identify defects adversely affecting OPC features.

BRIEF DESCRIPTION OF THE DRAWINGS

FIGS. 10A(1–3) illustrate simulated wafer images of a defect-free area of the physical mask in FIG. 9A for three exposures.

FIGS. 10B(1–3) illustrate simulated wafer images of a defect-free area of the reference mask in FIG. 9B for three exposures.

FIGS. 11A(1–3) illustrate simulated wafer images of a defect area of the physical mask in FIG. 9A for three exposures.

FIGS. 11B(1–3) illustrate simulated wafer images of a defect area of the reference mask in FIG. 9B for three exposures.

DETAILED DESCRIPTION OF THE DRAWINGS

Introduction

In accordance with an inspection system/process, all irregularities, i.e. potential defects, are characterized as actual defects. In one embodiment, a severity score is provided for each defect, thereby giving a customer meaningful information to accurately assess the consequences of using a mask or repairing that mask. The defect severity score is calculated based on a number of factors relating to the changes in the critical dimensions of features proximate to the defect. In another embodiment, process windows can be used to provide objective information regarding mask defect printability. Certain other aspects of the mask relating to mask quality, such as line edge roughness and contact corner rounding, can also be quantified.

Layout of the IC: Identify Critical Regions

Figure 3:
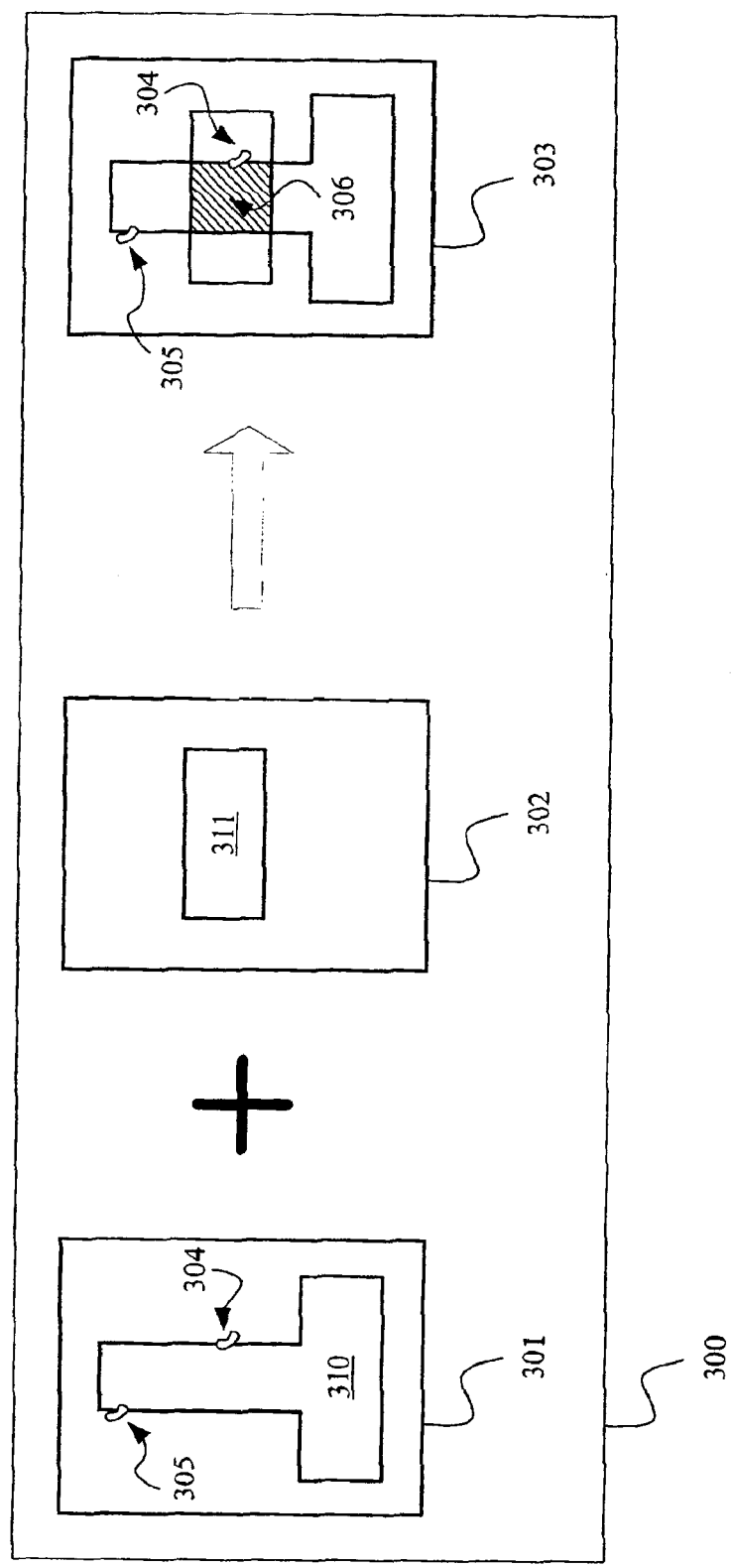
FIG. 3 illustrates a method of analyzing defects by using multiple masks.

FIG. 3 illustrates a feature that facilitates identifying critical regions of an IC. Specifically, a simplified process 300 includes identifying a defect in a mask and using at least one other mask to determine whether the defect is located in a critical region. For example, mask 301 represents a polysilicon region 310 of one layer in an IC. Two defects 304 and 305 are identified on polysilicon region 310. Note that both defects are identical in size. Mask 302 represents a diffusion region 311 of another layer in the IC.

Process 300 includes determining the size and location of the defects in relation to features in various masks, such as masks 301 and 302. For example, defects 304 and 305, when viewed solely with respect to polysilicon region 310 on mask 301, could be deemed insubstantial by a prior art inspection device, which typically determines defects by size. In contrast, process 300, in addition to size, considers the location of defects 304 and 305 in relation to diffusion region 311 provided on mask 302. Specifically, process 300 uses information from various masks to identify critical regions of the IC. A composite IC layout 303 identifies the overlap of polysilicon region 310 and diffusion region 311 as a critical region 306. As a key feature of the final IC, critical region 306, i.e. a gate, requires a high degree of precision to ensure proper performance of the transistor in the final IC device. Thus, by analyzing multiple masks and the features therein, defect 305 could be characterized as insubstantial because it is small and in a non-critical region (e.g. the interconnect), whereas defect 305 could be characterized as substantial even though it is small because it is in a critical region of the IC (e.g. the gate).

As described below in detail, a defect in a critical region will typically have a higher defect severity score than a defect in a non-critical region.

CD Variations: Identify Defect and Neighboring Features

Figure 4:
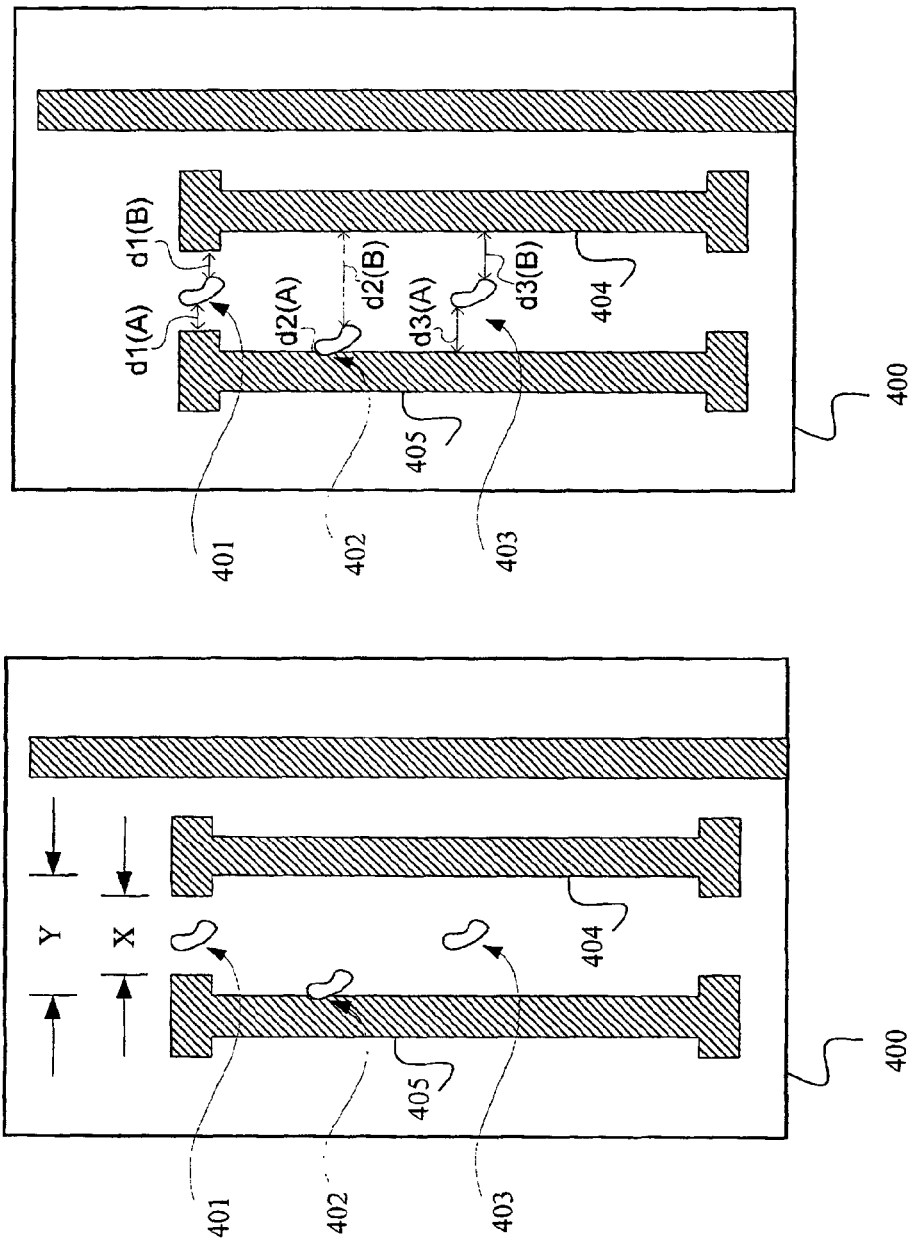
FIGS. 4A and 4B illustrate analyzing defects based on their location in relation to various features on the mask.

FIG. 4A illustrates a simplified mask 400 representing various polysilicon features of one layer in an IC. Mask 400 includes three defects 401, 402, and 403 that might affect neighboring polysilicon features 404 and 405. In this example, assume that defects 401, 402, and 403 are identical in size.

In general, a defect typically has more impact in a crowded region than in a less-crowded region. Thus, a defect located in an-area defined by features a distance X apart can have more printability impact than a defect located in an area defined by features distance Y apart, assuming that distance X is less than distance Y. However, this general rule has significant limitations.

Referring to FIG. 4B, each defect can be analyzed according to its location relative to neighboring features. For example, assume that defect 401 is located a distance d1(A) from feature 405 and a distance d1(B) from feature 404, wherein distance d1(A) is substantially equal to distance d1(B). Assume further that defect 403 is located a distance d3(A) from feature 405 and a distance d3(B) from feature 404, wherein distance d3(A) is substantially equal to distance d3(B). In this example, defect 401 would have a greater printability impact on mask 400 than defect 403. Therefore, the general rule applies to defects 401 and 403.

However, mask 400 also includes a defect 402 located a distance d2(A)(i.e. zero) from feature 405 and a distance d2(B) from feature 404. In this case, defect 402 could have more printability impact on feature 405 than defect 401. Moreover, defect 402 probably has less printability impact on feature 404 than defect 403. Thus, a general rule limited to the spacing of features does not provide an accurate indication of printability impact.

One possible solution to this problem is to measure the distances to neighboring features (such as d1, d2, and d3) from each defect (such as defects 401, 402, and 403, respectively). These distances in combination with a measurement of the size of the defect could be factored into a plurality of design rules to provide the printability impact. However, this analysis is computationally intensive, thereby increasing the time required to provide meaningful information to the customer. Moreover, even if the size of the defect and the distance of the defect from the neighboring feature are known, the actual impact of the defect on the neighboring feature cannot fully be predicted by mere inspection of the mask.

Defect Printability Analysis

Therefore, in accordance with one embodiment, a limited number of variables are analyzed. In one embodiment, this limited number of variables includes the critical dimension (CD) of the mask. Specifically, any CD changes in features that occur because of the proximity of a defect can be determined. To analyze these CD changes, the mask image can be simulated, as described in reference to FIG. 5.

Figure 5:
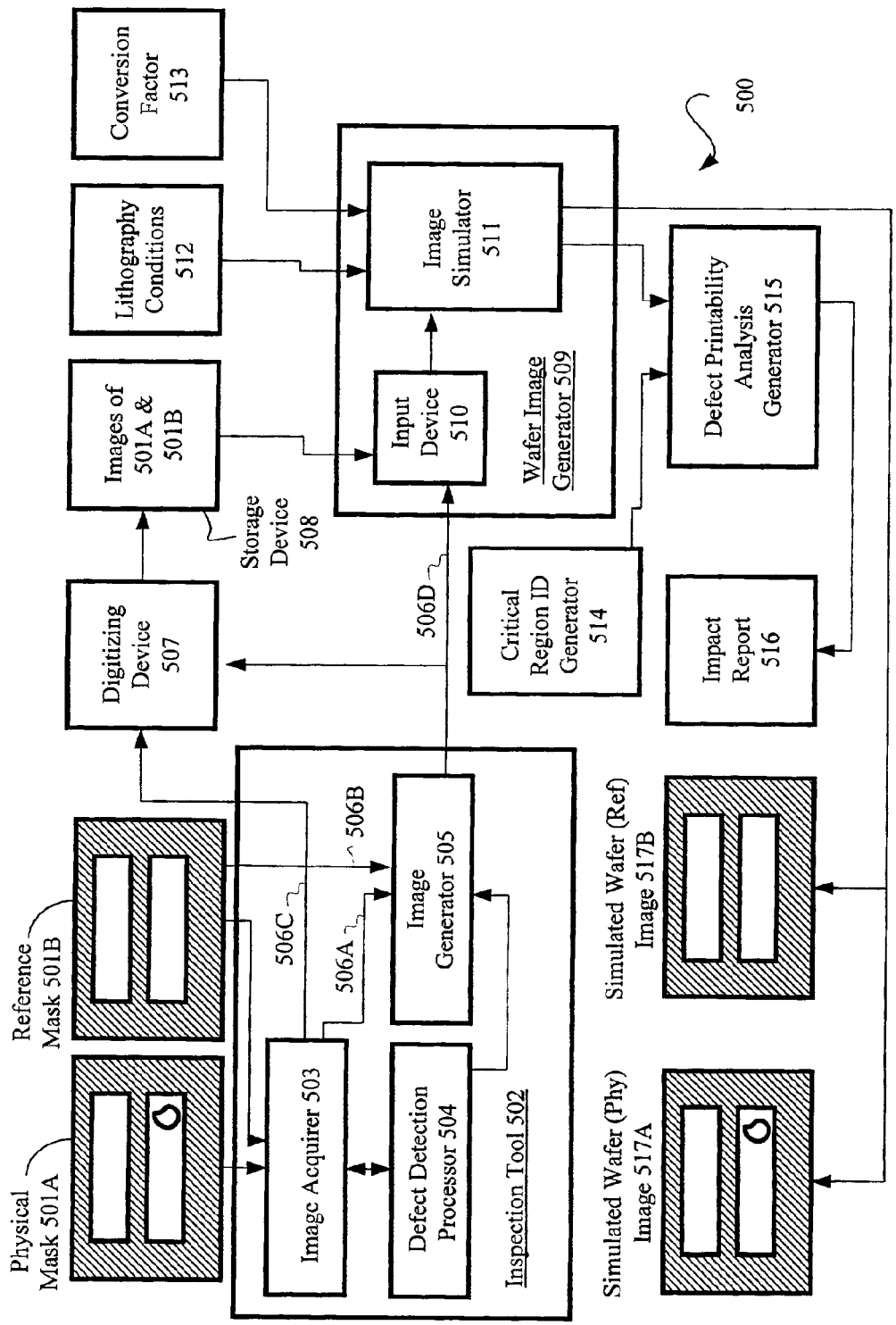
FIG. 5 illustrates a mask inspection process and system.

FIG. 5 illustrates a process 500 for analyzing defect printability. In process 500, a physical mask 501A and a reference mask 501B are analyzed by an inspection tool 502. In one embodiment, reference mask 501B can be a physical mask having the same layout as physical mask 501A, but having no defects. In another embodiment, reference mask 501B can be a simulated image from a layout of physical mask 501A.

In one embodiment, an inspection tool 502 includes an image acquirer 503 to scan all or a portion of a physical mask 501A and corresponding portions of reference mask 501B. Image acquirer 503 may include a high-resolution imaging device such as a high-resolution optical microscope, a scanning electron microscope (SEM), a focus ion beam, an atomic force microscope, or a near-field optical microscope. Image acquirer 503 may also include an interface device for digitizing the image information from the imaging device. In one embodiment, the interface device includes a CCD camera that generates a gray scale bit image that represents the image.

A defect detection processor 504 compares the images from physical mask 501A and reference mask 501B provided by image acquirer 503 and identifies any defects of physical mask 501A. In one embodiment, defect detection processor 504 includes a computer running a program of instructions for scanning masks 501. If a defect is identified, defect detection processor 504 signals an image generator 505 to provide an image of the defect and the area surrounding the defect from physical mask 501A as well as the corresponding area from reference mask 501B. Image generator 505 also provides an image of a defect-free area from both masks 501. In one embodiment, image generator 505 can provide an image including both the defect area and the defect-free area. To facilitate the defect printability analysis described below in detail, the coordinates of these defect and defect-free areas can be transmitted with the generated area image data. Note that if reference mask 501B is provided as a simulated layout and if a complete image of physical mask 501A is to be generated, then the simulated layout file of reference mask 501B can be provided directly to image generator 505 as indicated by line 506B.

In one embodiment, inspection tool 502 then provides both area image data from physical mask 501A and reference mask 501B to a wafer image generator 509 in a real-time data feed, as indicated by line 506D. In another embodiment, this data is digitized by digitizing device 507, stored in a storage device 508, and then provided to wafer image generator 509 at a later point in time. Storage device 508 can store this digitized information in a format such as Windows BMP on any type of appropriate media including a computer hard disk drive, a CDROM, and a server. In yet another embodiment that analyzes physical mask 501A in its entirety, the scanned image(s) provided by image acquirer 503 can be provided to image generator 505 as indicated by line 506A or to digitizing device 507 as indicated by line 506C.

Wafer image generator 509 includes an input device 510 and an image simulator 511. Input device 510 typically includes hardware for reading the type of image data from inspection tool 502 and/or from storage device 508, such as any known, digitizing image grabber (for a real-time data feed) provided by Matrox™, Meteor™, or Pulsar™. In one embodiment, image simulator 511 includes a computer-implemented program running Windows/DOS at 200 MHz on an appropriate platform, such as a personal computer or a workstation, having at least 64 MB of memory. Image simulator 511 receives the image data from input device 510 and generates simulations of the image data, i.e. for physical mask 501A and reference mask 501B. These simulations are referenced herein as wafer image (Phy) (for physical mask) 517A and wafer image (Ref) (for reference mask) 517B.

In one embodiment, image simulator 511 further receives a plurality of lithography conditions 512. These conditions include data that is specific to the lithography conditions and system parameters under which physical mask 501A will be exposed by the customer. Such data could include, for example, the wavelength of the illumination being used in the system ($\lambda$), the numerical aperture of the system (NA), the coherency value of the system ($\sigma$), the type of illumination (e.g. off-axis or annular), the defocus, the exposure level, the lens aberrations, the substrate conditions, and the critical dimension (CD) of the design. In one embodiment, each parameter could include a range of values, thereby allowing image simulator 511 to generate a plurality of simulations based on a range of possible lithography conditions in different combinations. For example, this could be done by Monte Carlo simulation with different types of distribution, such as Gaussian distribution. Thus, wafer image (Phy) 517A and wafer image (Ref) 517B can represent the simulated images which physical mask 501A and reference mask 501B (or portions thereof) would generate if an optical lithography exposure had been performed under the same conditions as lithography conditions 512.

Conversion Factors

For above (or near) wavelength designs, design rules for features used in the layout can typically scale simultaneously by the same factor. In the event that some rules do not scale as fast as the other rules, minor modifications, typically performed within a relatively short time, can be made to the database. However, in contrast, manufacturing steps in sub-wavelength production flow are highly non-linear. Specifically, any mask errors can be amplified in the printed pattern on the wafer, and consequently can adversely affect final device performance.

Therefore, to enhance the accuracy of wafer images 517 in sub-wavelength technology, image simulator 511 can also receive a conversion factor 513 in accordance with one embodiment. In one instance, the conversion factor is called a mask error enhancement factor (MEEF).

If the conversion factor is "known", then a multiplication of the mask CDs by the conversion factor can be done. Currently, "known" conversion factors are typically theoretical estimations. However, these theoretical estimations can be inaccurate for a number of reasons. First, as recognized by Applicants, the conversion factor can vary based on features on the mask. For example, the conversion factor for isolated lines can be different from the conversion factor of densely packed lines. Moreover, the conversion factor for a contact can be different from the conversion factors of either isolated lines or densely packed lines. Second, in addition to design issues on the mask, all aspects of the fabrication process including the stepper and the photoresist, for example, can affect the conversion factor for a particular feature on the mask. Therefore, theoretical estimations, which fail to account for design issues and process parameters, are inherently inaccurate.

Alternatively, if theoretical estimations are not accurate, then actual wafers can be fabricated and the device CDs can be measured on the wafer using SEM to determine the conversion factor(s). However, this process typically includes printing and measuring tens or even hundreds of mask features to measure and calculate the conversion factor(s). Therefore, this process is extremely expensive and, thus, commercially impractical.

Figure 6:
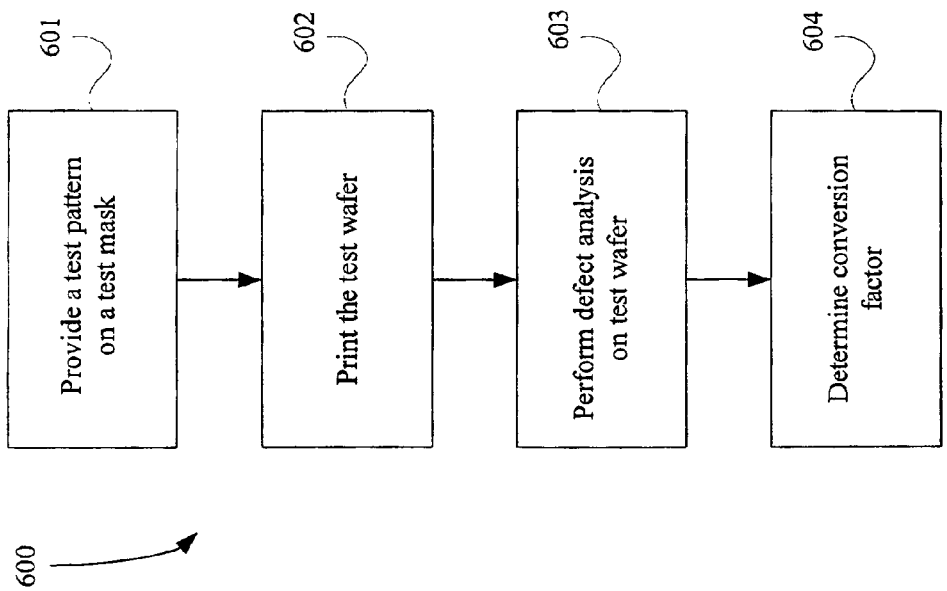
FIG. 6 illustrates one method to generate accurate conversion factors.

A number of cost-effective solutions to the above-described problems can be provided. FIG. 6 illustrates one method 600 to generate accurate conversion factors. In method 600, a test pattern can be provided on a test mask in step 601. The test pattern could include isolated lines of varying widths, densely packed lines of varying widths, and contacts of various sizes. At this point, a single wafer can be printed in step 602. Defect analysis, including any changes in CD, can be noted for each test pattern on the wafer in step 603. From this information, the conversion factor for each feature can be accurately calculated in step 604. A limited number of additional wafers can also be printed using various processes to obtain the conversion factors for these fabrication processes.

Note that the wafer printed from the test mask also includes shop-specific information, which could affect the conversion factor. Specifically, process variations can, and typically do, vary from one shop to another shop. This variation can result in some CD changes on the wafer, which is generally termed "bias" in the industry. By printing a wafer or a limited number of wafers at the shop and using a test mask as described above, a customer can either verify the shop's published bias or independently determine that shop's bias.

The test mask having the above-described test pattern provides the user with an accurate conversion factor as well as shop bias, thereby allowing the customer to potentially compensate for unacceptable CD changes (typically either in the design process, in the mask correction operation (described in further detail below), or by choosing a different shop).

Figure 7:
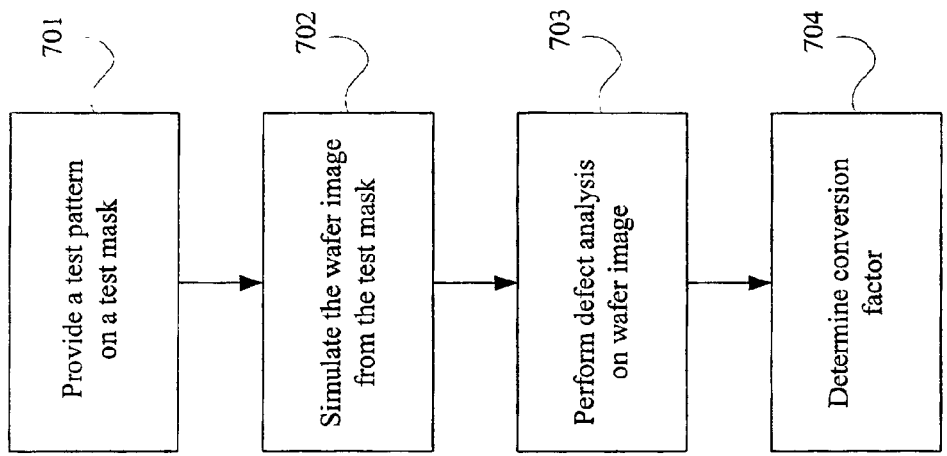
FIG. 7 illustrates another method to generate accurate conversion factors.

FIG. 7 illustrates another method 700 to generate accurate conversion factors. In method 700, a test pattern can be provided on a test mask in step 701. Similarly to method 600, this test pattern could also include isolated lines of varying widths, densely packed lines of varying widths, and contacts of various sizes. At this point, a wafer image from the test mask can be simulated in step 702 using image simulator 511 (FIG. 5). Defect analysis, including any changes in CD (explained in detail below), can be noted for each test pattern on the simulated wafer image in step 703. From this information, the conversion factor for each feature can be accurately calculated in step 704. Note that any number of additional masks can be simulated using various processes (e.g. lithography conditions 512) to obtain the conversion factors for these fabrication processes. Further note that the shop bias, described in reference to FIG. 6, can also be included in lithography conditions 512, thereby further enhancing the accuracy of the conversion factors generated by this embodiment.

Method 700 is extremely cost-effective because it eliminates the cost associated with the printed wafer as well as the time for fabrication of that wafer. Moreover, because of the simulation environment, method 700 provides significant flexibility in optimizing system parameters before actual fabrication.

Image Simulation

Image simulator 511 approximates the process of optical lithography by using a simplified version of the Hopkins model as applied to integrated circuit patterns. In this simplified version, the Hopkins model is viewed as a plurality of low pass filters that are applied to the input data. The output images from those low pass filters are added to generate the simulated images (i.e. simulated wafer (Phy) image 517A and simulated wafer (Ref) image 517B). Additional information regarding the Hopkins model as used by image simulator 511 is provided in U.S. Ser. No. 09/130, 996, and therefore is not described in detail herein.

Defect Severity Score Calculation

A defect printability analysis generator 515 receives simulated wafer images 517 from image simulator 511. Generator 515 includes a computer-implemented program running Windows/DOS at 200 MHz on an appropriate platform, such as a personal computer or a workstation, having at least 64 MB of memory. In one embodiment, image simulator 511 and generator 515 run on the same platform.

Figure 8A:
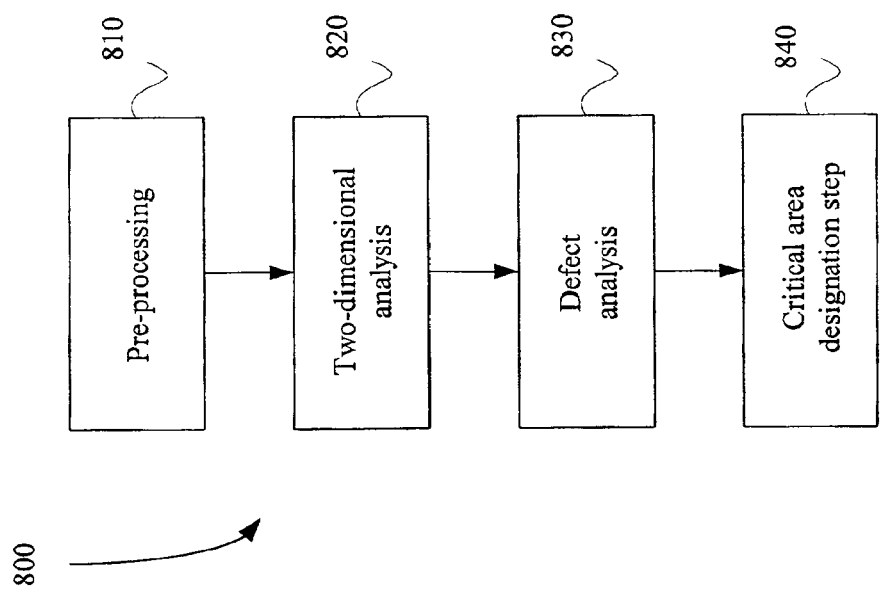
FIGS. 8A–8C illustrate various features of a computer-implemented program associated with the defect printability analysis generator.
Figures 8B, 8C:
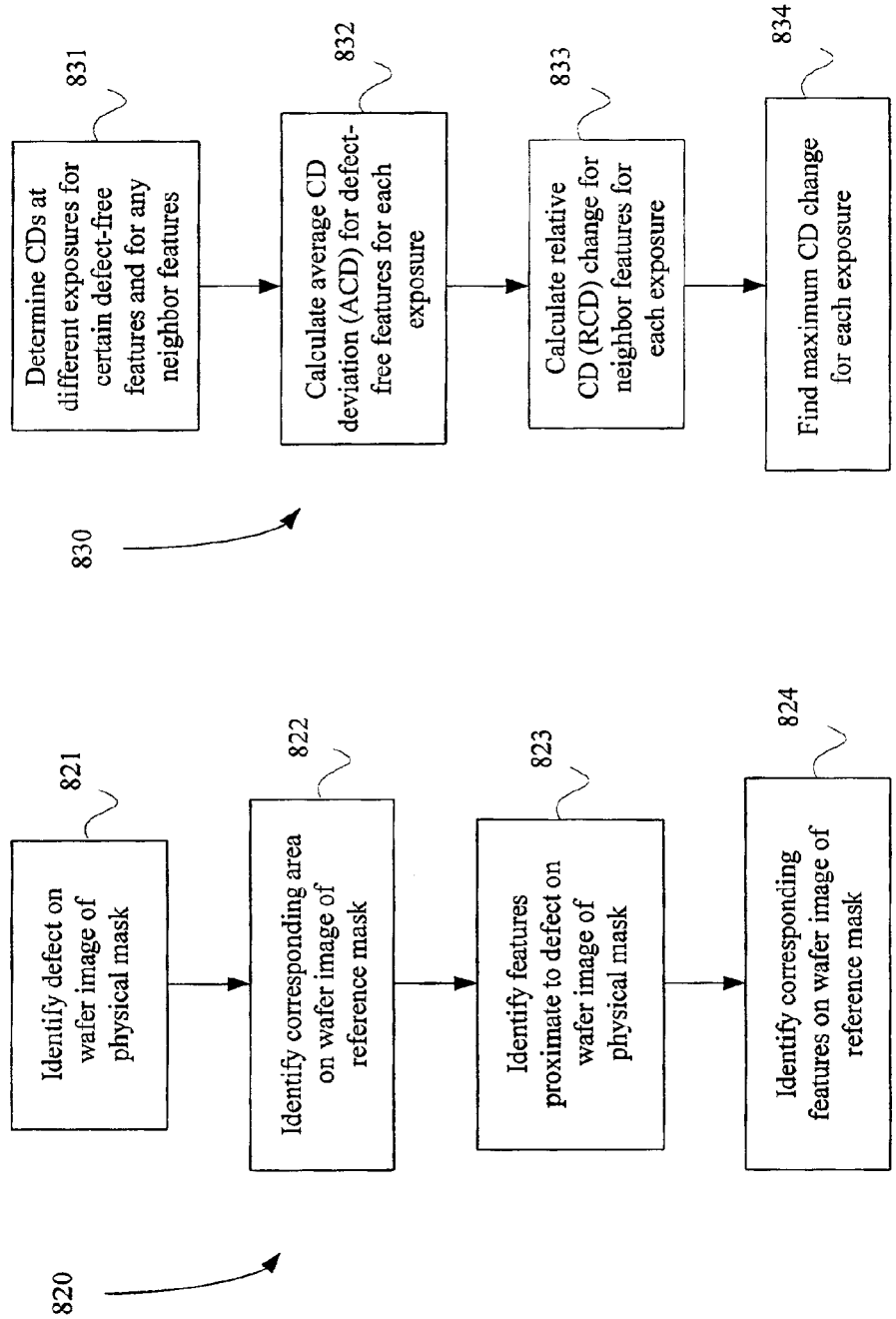

FIGS. 8A–8C illustrate various features of the computer-implemented program associated with generator 515. FIG. 8A indicates that a method 800 of generating a defect severity score includes a pre-processing step 810, a two-dimensional analysis step 820, a defect analysis step 830, and a critical area designation step 840.

In pre-processing step 810, simulated wafer (Phy) image 517A and simulated wafer (Ref) image 517B are aligned. Alignment can be done using defect-free patterns (assuming the simulated images 517 include both defect and defect-free areas) or the coordinates provided by image generator 505 for the defect/defect-free areas (and subsequently transmitted to input device 510, image simulator 511, and finally defect printability analysis 515). When these patterns/areas are aligned, the features provided on simulated images 517 are also aligned.

After alignment, two-dimensional analysis step 820 can proceed. Specifically referring to FIG. 8B, which describes two-dimensional analysis step 820 in further detail, a defect on simulated wafer (Phy) image 517A is identified in step 821. Then, the corresponding area of simulated wafer (Ref) image 517B is identified in step 822. Note that the coordinates provided by image generator 505 can be used for identification steps 821 and 822. In step 823, any feature proximate to the defect (also referenced herein as a neighbor feature) on simulated wafer (Phy) image 517A is identified. Finally, in step 824, the corresponding feature(s) on simulated wafer (Ref) image 517B can be identified.

Note that the term "proximate" can refer to any feature that changes in CD as a result of the proximity of the defect. However, in one simple implementation, any feature within a predetermined distance of the defect can be identified as a neighbor feature. In another embodiment, both the size of the defect (which can be determined in step 821) and the distance of the defect from the neighbor feature (which can be determined in step 823) are compared to measurements in a design rule table. The design rule table can identify, for each defect size (or range of sizes), a maximum distance from the defect, wherein if the feature is located less than the maximum distance from the defect, then the feature is characterized as a neighbor feature.

After two-dimensional analysis, defect analysis step 830 can proceed. In defect analysis, the defect-free areas are analyzed to calculate average CD deviations (ACDs) (explained in detail below) and the defect areas are analyzed to calculate the relative CD deviations (RCDs) (also explained in detail below). Note that calculating the ACDs and RCDs can be done in any order. FIG. 8C describes defect analysis step 830 in further detail. Specifically, in step 831, CDs for one or more features in the defect-free areas on the simulated wafer images 517 and for any neighbor features in the defect areas on the simulated wafer images 517 are measured.

To determine an ACD, the CD of one defect-free feature on simulated wafer image (physical mask) 517A is first subtracted from the CD of the corresponding defect-free feature on simulated wafer image (reference mask) 517B. This difference is then divided by the CD of the same defect-free feature on simulated wafer image (reference) 517B. To improve the accuracy of the ACD calculation, multiple features can be analyzed. Specifically, N ACDs can be added and then divided by N, wherein N is an integer greater than or equal to 1. For example, if two features were analyzed, then the ACD could be calculated by the following equation:

$$[(CD(R1)-CD(P1))/CD(R1)+[(CD(R2)-CD(P2))/CD(R2)]/2),$$

wherein R represents the simulated wafer image of the reference mask and P represents the simulated wafer image of the physical mask. Note that ACDs could be determined for different defect-free features or for the same defect-free feature. For example, in one embodiment, a representative gate can be cut every 2 nm (parallel slices of FET channel) across the gate width. Note that the CD estimation can be performed using standard mask inspection equipment provided by KLA-Tencor, Applied Materials, LaserTech, or any other reticle inspection/metrology tool vendor.

In one embodiment, different exposures can be used to provide multiple ACDs for each feature. Note that the exposures used can be a range of values that deviate from the exposure level that will be used in the actual fabrication process, thereby providing a user with valuable information regarding the worst-case result. Further note that such exposure conditions are typically included in lithography conditions 512 (FIG. 5) that can be simulated. Therefore, referring back to FIG. 8C, the ACD for each exposure can be calculated in step 832.

In step 833, a relative CD deviation (RCD) is calculated for each identified neighbor feature (as identified in the defect areas of the simulated images) in each exposure. For example, for each exposure, the CD of an identified neighbor feature (such as 904(R)) in defect area 901(R) of simulated wafer image 901(R) is subtracted from the CD of the same feature (in this case, 904(P)) in defect area 901(P) on simulated wafer image 901(P). This difference is then divided by the CD of the identified neighbor feature on simulated wafer image 901(R) (i.e. (CD(P)−CD(R))/CD(R). Finally, the maximum RCD (MCD) of the identified neighbor feature can be determined for each exposure in step 834.

As described in reference to FIG. 3, a feature in a critical region, such as a gate, requires a high degree of precision to ensure proper performance of the transistor in the final IC device. Thus, by analyzing multiple masks and the features therein, a defect could be characterized as insubstantial because it is small and in a non-critical region (e.g. the interconnect), whereas a defect could be characterized as substantial even though it is small because it is in a critical region of the IC (e.g. the gate).

Referring to FIG. 5, defect printability analysis generator 515 also receives information from a critical region identification generator 514. Critical region identification generator 514 could include any standard pattern recognition tools (both hardware and software) to analyze the physical masks, like physical mask 501A, used to fabricate the IC. Irrespective of specific tools used, critical region identification generator 514 provides defect printability analysis generator 515 with information identifying areas of each mask that are designated critical regions. With this information, defect printability analysis generator 515 can determine whether a defect is located within a critical region in step 840 (FIG. 8A).

A defect in a critical region will typically have a lower tolerance for relative CD changes. In one embodiment, the tolerance for CD changes (TCD) could be provided by a look-up table. This look-up table could include values determined by a mask quality control engineer based on experience and various mask specifications. For example, a critical area could have a TCD range between approximately 3% and 5%, whereas a non-critical area with very few features could have a TCD range between approximately 10% and 15%. In one embodiment, critical region ID generator 514 could include this look-up table.

Equation 1 provides an illustrative calculation for determining a defect severity score. Note that Equation 1 includes the ACD, MCD, and TCD variables described in detail above, and further includes a variable i that indicates a particular exposure and a variable N that indicates the total number of exposures analyzed.

$$DSS = (3/N) \times \sum_{1}^{N} (MCD_i - ACD_i/3)/TCD \quad \text{Equation 1}$$

Figure 9A:
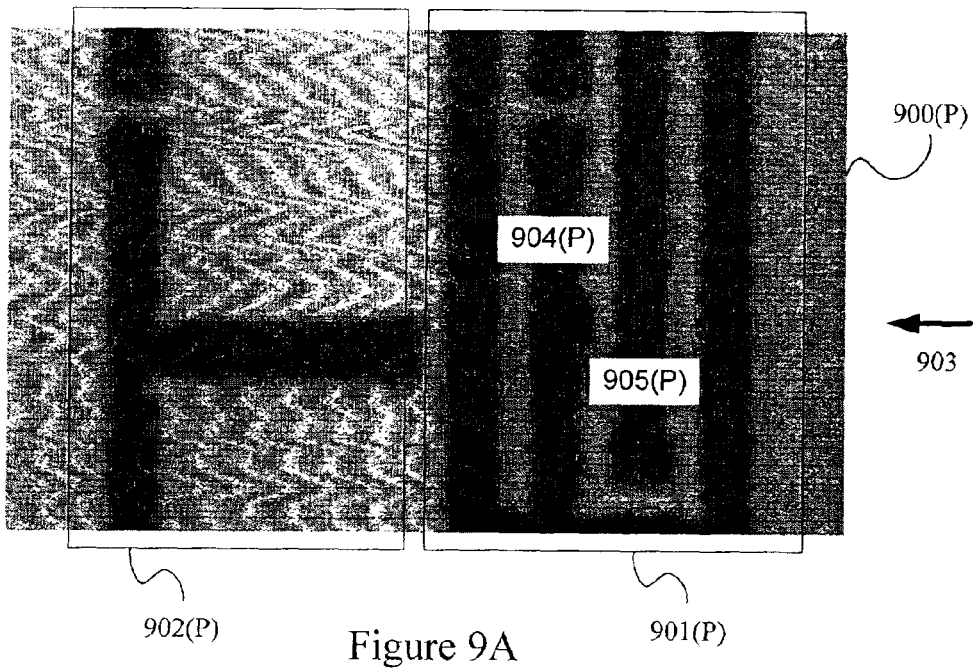
FIGS. 9A and 9B illustrate portions of a physical mask and a reference mask, respectively.
Figure 9B:
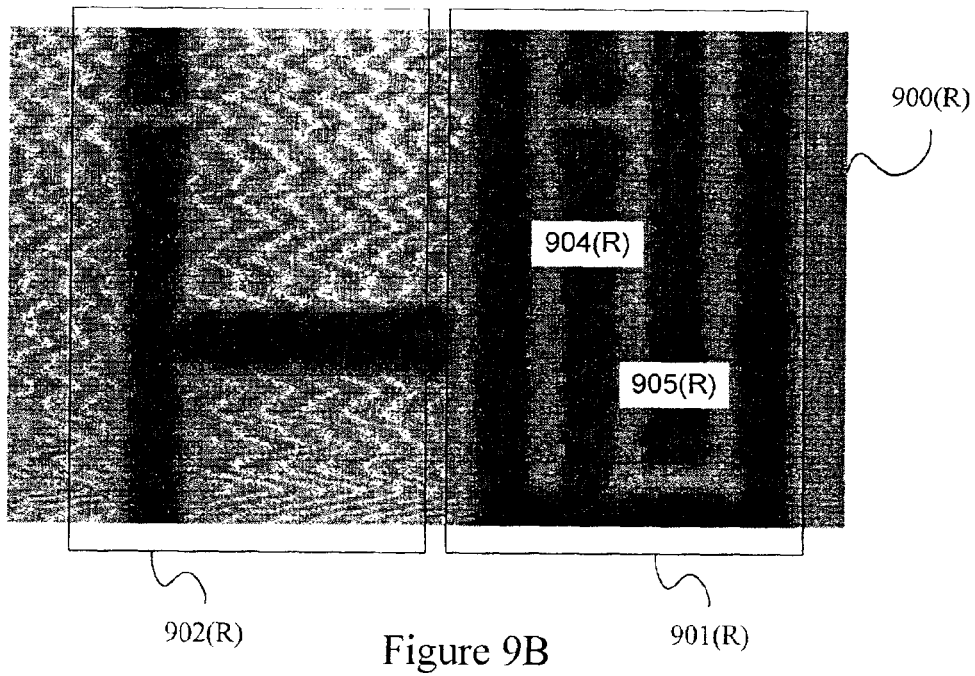

FIG. 9A illustrates an exemplary portion 900(P) from a physical mask. Portion 900(P) includes a defect area 901(P) and a defect-free area 902(P). In a similar manner, FIG. 9B illustrates a portion 900(R) from a reference mask corresponding to portion 900(P). Portion 900(R) includes a defect area 901(R) and a defect-free area 902(R).

By using coordinates or defect-free patterns in pre-processing step 810, the corresponding locations of these portions/areas in the simulated wafer images can be aligned. Specifically, for example, the simulated wafer images of defect-free areas 902(P) and 902(R) can be aligned. In a similar manner the simulated wafer images of defect areas 901(P) and 901(R) can be aligned. Once areas 901 and 902 are aligned, the features in the simulated wafer images are also aligned. Thus, for example, features 904(P) and 905(P) of defect area 901(P) are aligned with features 904(R) and 905(R) of defect area 901(R) in pre-processing step 810.

In two-dimensional analysis step 820, a defect on the simulated wafer image of mask portion 901(P) is identified. In this example, an arrow points to a defect 903 in defect area 901(P). Features 904(P) and 905(P) are then identified as neighbor features that can be affected by defect 903. Finally, any corresponding features on the simulated wafer image of mask portion 901(R) can be identified. In this example, features 904(R) and 905(R) are identified.

At this point, defect analysis step 830 can proceed. FIGS. 10 (A(1)–A(3) and B(1)–B(3)) and 11 (A(1)–A(3) and B(1)–B(3)) illustrate the application of the defect severity score calculation to the simulated wafer images of portions 900(P) and 900(R). To calculate the average CD deviations for defect-free features, multiple features are typically measured. For example, FIGS. 10A(1–3) represent the simulated wafer images from defect-free area 902(P) of physical mask 900(P) for three exposures. Lines 1001(P)–1006(P) represent cuts made to two defect-free features of the simulated wafer image in the three exposures. Specifically, lines 1001(P) and 1002(P) represent cuts made to two features in a first exposure, lines 1003(P) and 1004(P) represent the same cuts made to the same features in a second exposure, and lines 1005(P) and 1006(P) represent the same cuts made to the same features in a third exposure.

In a similar manner, FIG. 10B(1–3) represent simulated wafer images from defect-free area 902(R) of reference mask 900(R) for the same three exposures. Lines 1001(R)–1006(R) represent cuts made to two defect-free features of the simulated wafer image in the three exposures, wherein these cuts correspond to the cuts 1001(P)–1006(P). Thus, lines 1001(R) and 1002(R) represent cuts made to two features in a first exposure, lines 1003(R) and 1004(R) represent the same cuts made to the same features in a second exposure, and lines 1005(R) and 1006(R) represent the same cuts made to the same features in a third exposure.

Each cut line 1001(P)–1006(P) and 1001(R)–1006(R) provides an associated CD. Therefore, for ease of reference, lines 1001(P)–1006(P) and 1001(R)–1006(R) are hereinafter referenced as CDs 1001(M)–1006(M) and 1001(R)–1006(R).

For the first exposure shown in FIGS. 10A(1) and 10B(1), the average CD deviation can be calculated as follows:

$$ACD(1)=[(1001(R)-1001(P))/1001(R)+(1002(R)-1002(P))/1002(R)]/2$$

In one embodiment, the actual measurements of CDs 1001(R), 1001(P), 1002(R), and 1002(P) are, respectively, 266 nm, 266 nm, 322 nm, and 294 nm. Plugging these values into the equation for ACD(1), yields approximately 0.043 nm.

For the second exposures shown in FIG. 10A(2) and 10B(2), the average CD deviation can be calculated in a similar manner:

$$ACD(2)=[(1003(R)-1003(P))/1003(R)+(1004(R)-1004(P))/1004(R)]/2$$

In one embodiment, the actual measurements of CDs 1003(R), 1003(P), 1004 (R), and 1004(P) are, respectively, 266 nm, 266 nm, 294 nm, and 294 nm. Plugging these values into the equation for ACD(2), yields 0.0 nm.

Finally, for the third exposure shown in FIGS. 10A(3) and 10B(3), the average CD deviation can also be calculated in the same manner:

$$ACD(3)=[(1005(R)-1005(P))/1005(R)+(1006(R)-1006(P))/1006(R)]/2$$

In one embodiment, the actual measurements of CDs 1005(R), 1005(P), 1006(R), and 1006(P) are, respectively, 252 nm, 238 nm, 294 nm, and 294 nm. Plugging these values into the equation for ACD(3), yields approximately 0.028 nm.

In defect analysis, a relative CD deviation (RCD) is also calculated for neighbor features in the defect area for each exposure level. FIGS. 11A(1–3) illustrate the simulated wafer images for features 904(P) and 905(P) in defect area 901(P) for three exposures. Lines 1101(P)–1106(P) represent cuts made to these two features of the simulated wafer image in the three exposures. Specifically, lines 1101(P) and 1102(P) represent cuts made to features 904(P) and 905(P) in a first exposure, lines 1103(P) and 1104(P) represent cuts made to features 904(P) and 905(P) in a second exposure, and lines 1105(P) and 1106(P) represent cuts made to features 904(P) and 905(P) in a third exposure.

Similarly, FIGS. 11B(1–3) illustrate the simulated wafer images for features 904(R) and 905(R) for the same three exposures. Lines 1101(R)–1106(R) represent cuts made to these two features of the simulated wafer image in the three exposures. Specifically, lines 1101(R) and 1102(R) represent cuts made to features 904(R) and 905(R) in a first exposure, lines 1103(R) and 1104(R) represent cuts made to features 904(R) and 905(R) in a second exposure, and lines 1105(R) and 1106(R) represent cuts made to features 904(R) and 905(R) in a third exposure.

Each line 1101(P)–1106(P) and 1101(R)–1106(R) provides an associated CD. Therefore, for ease of reference, lines 1101(P)–1106(P) and 1101(R)–1106(R) are hereinafter referenced as CDs 1101(P)–1106(P) and 1101(R)–1106(R).

For the first exposures shown in FIG. 11A(1) and 11B(1), the relative CD deviation (RCD) can be calculated for feature 904 as follows:

$$RCD(1(904))=(1101(P)-1101(R))/1101(R)$$

In one embodiment, the actual measurements of CDs 1101(R) and 1101(P) are, respectively, 266 nm and 364 nm. Plugging these values into the equation for RCD(1(904)), yields approximately 0.368 nm.

In a similar manner, for the first exposures shown in FIGS. 11A(1) and 11B(1), the relative, maximum CD (RCD) change can be calculated for feature 905 as follows:

$$RCD(1(905))=(1102(P)-1102(R))/1102(R)$$

In one embodiment, the actual measurements of CDs 1102(R) and 1102(P) are, respectively, 252 nm and 322 nm. Plugging these values into the equation for RCD(1(905)), yields approximately 0.278 nm.

The RCDs can be calculated for features 904 and 905 for the second and third exposures in a similar manner as shown below.

$$RCD(2(904))=(1103(P)-1103(R))/1103(R)$$

$$RCD(2(905))=(1104(P)-1104(R))/1104(R)$$

$$RCD(3(904))=(1105(P)-1105(R))/1105(R)$$

$$RCD(3(905))=(1106(P)-1106(R))/1106(R)$$

In one embodiment, the actual measurements of CDs 1103(R), 1103(P), 1104(R), 1104(P), 1105(R), 1105(P), 1106(R), 1106(P) are, respectively, 238 nm, 350 nm, 252 nm, 294 nm, 224 nm and 280 nm. Plugging these values into the equations for RCD(2(904)), RCD(2(905)), RCD(3(904)), and RCD(3(905)), yields, respectively, approximately 0.471 nm, 0.167 nm, 0.353 nm, and 0.250 nm.

To determine the maximum CD deviation (MCD) for each exposure, the largest RCD value is chosen. Thus, the maximum CD deviation for the first exposure (MCD(1)) is 0.368 nm (0.368>0.278), MCD(2) is 0.471 nm (0.471>0.167), and MCD(3) is 0.353 nm (0.353>0.250).

The defect severity score (DSS) can be calculated by using Equation 1. In the example given, because three exposures were analyzed, N=3.

Substituting these values in Equation 1 yields:

$$DSS = (3/3) \times \sum_{1}^{3} (MCD_i - (ACD_i/3))/TCD$$

Thus, based on the three exposures, $$DSS=(3/3)[(MCD(1)-(ACD(1)/3))/TCD+(MCD(2)-(ACD(2)/3))/TCD+(MCD(3)-(ACD(3)/3))/TCD]$$

Substituting the values calculated above for MCD and ACD for the three exposures, yields:

$$DSS=[(0.368-(0.043/3))/0.1+(0.473-(0/3))/0.1+(0.353-(0.028/3))/0.1$$

$$DSS=3.54+4.73+3.44$$

Therefore, defect 903 (see FIG. 9A) has a DSS of approximately 11.71.

Defect printability analysis generator 515 (FIG. 5) can output the defect severity score (DSS)(in one embodiment, a scale from 1 to 10) in an impact report 516. This impact report 516 can be used to reduce human error in defect printability analysis. For example, perhaps a DSS score of 5 indicates that printed features would have significant performance issues, but that repair of the physical mask is possible. On the other hand, perhaps a DSS score of 7 and above indicates not only performance issues, but that re-fabrication of the physical mask is recommended. For example, in one embodiment, a DSS of less than 3 means that the CD changes due to the defect are within the specified CD tolerance, a DSS between 3 and 6 means that the CD changes due to the defect are larger than the specified CD tolerance, but the CD changes do not result in severe defects on the wafer (such as opens or bridges), and a DSS greater than 6 means that the CD changes due to the defect result in severe defects on the wafer. Thus, by providing a numerical result having an associated meaning for each number, a technician can proceed efficiently and without error to the next action, e.g. repair of the physical mask or re-fabrication of the physical mask.

Process Windows

Defect printability can also be assessed using various process windows. Process windows can be derived from certain plots known by those skilled in the art. In general terms, the process window of a feature is the amount of variation in the process that can be tolerated while still maintaining critical dimensions (CDs) of the feature within a certain range of the target CD.

One known process variation is the focus setting of the projection tool, i.e. the stepper. The focus can significantly change the resist profile (CD, sidewall angle, and resist thickness) and thus is critical in providing an acceptable lithographic process.

Because of the impact of focus and exposure, these variables are typically varied at the same time in a focus-exposure matrix. The process window can be derived from such a matrix. Focus and exposure values that fall within the process window produce resist features, e.g. CDs, within tolerance, whereas focus and exposure values that fall outside the process window produce resist features outside tolerance. Thus, as shown in detail below, the process window can provide an objective means for determining the severity and printability of a defect.

Figure 12B:
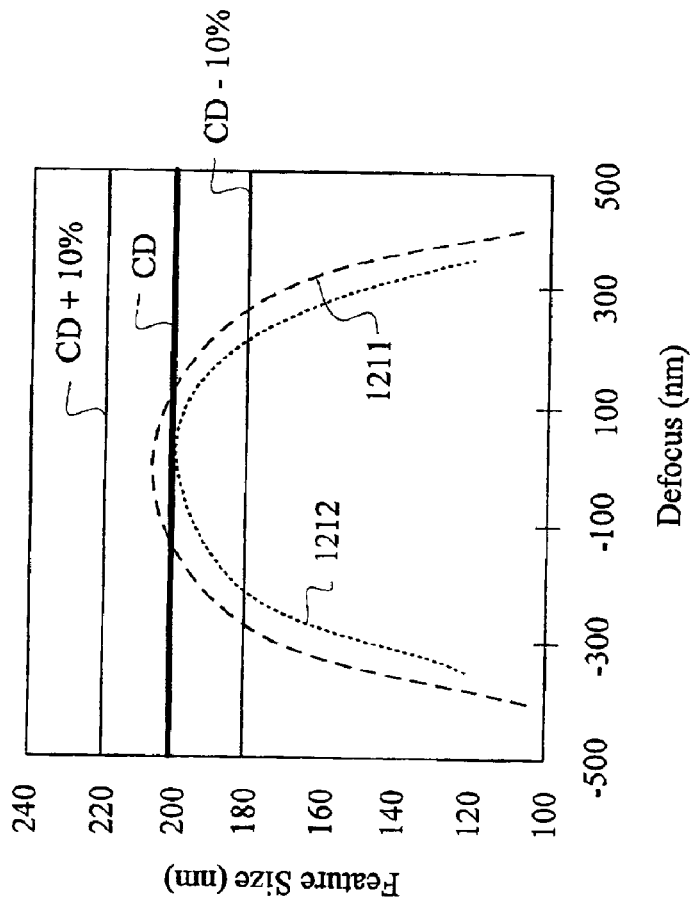
FIG. 12B illustrates a plot of feature size versus defocus for the feature of FIG. 12A.
Figure 12A:
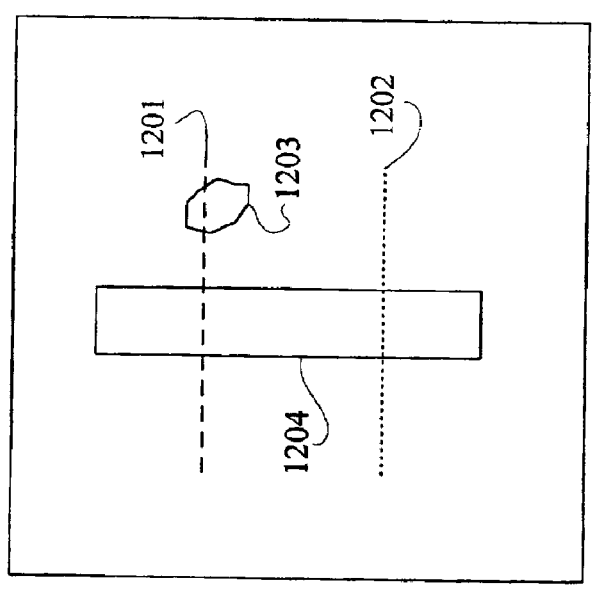
FIG. 12A illustrates a mask including a feature and a defect proximate to the feature.

For example, FIG. 12A illustrates a mask having a feature 1204 and a defect 1203. As shown above, defect 1203 will affect the width of feature 1204. Specifically, the width of feature 1204 at cut line 1201 will be larger than the width at cut line 1202.

FIG. 12B shows a plot of feature size (also in nanometers) versus defocus (in nanometers). In this figure, the bold horizontal line indicates that the target CD is 200 nm, whereas the other horizontal lines indicate a +/− 10% error of this target CD. Curves 1211 and 1212 are generated by exposing (or simulating exposure of) the mask including defect 1223 and analyzing the CDs of the printed feature at cut lines 1201 and 1202 at various defocus levels (in this case, −500 nm to 500 nm). Curves 1211 and 1212 represent the CD analysis at cut lines 1201 and 1202, respectively.

Logically, each feature size on curve 1212 has a corresponding larger feature size on curve 1211. For example, at −300 nm defocus, the feature size at cut line 1202 (see curve 1212) is approximately 150 nm, whereas the feature size at cut line 1201 (see curve 1211) is approximately 170 nm. Note that an acceptable defocus window for both curves, i.e. between horizontal lines CD +/− 10%, is between approximately −208 nm and 208 nm.

Figure 12D:
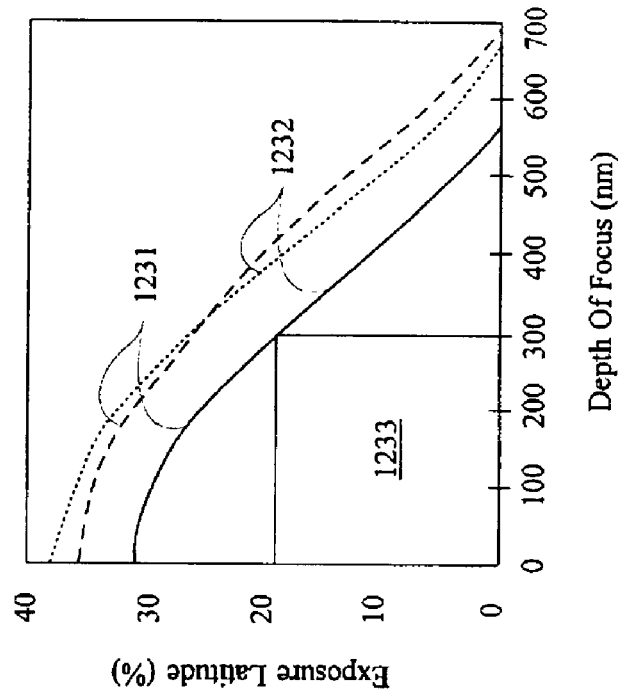
FIG. 12D illustrates a plot of exposure latitude versus depth of focus for the feature of FIG. 12A.
Figure 12C:
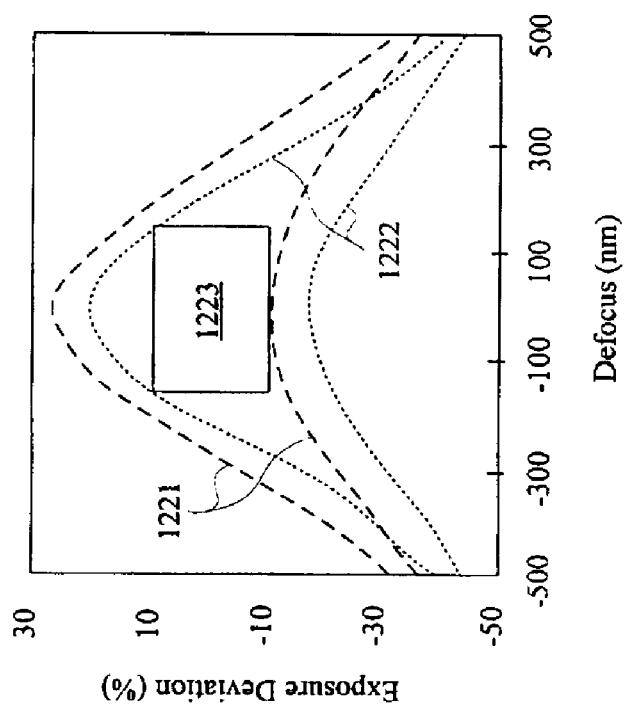
FIG. 12C illustrates a plot of exposure deviation versus defocus and a common process window plot for the feature of FIG. 12A.

FIG. 12C illustrates a plot of percentage exposure deviation versus defocus (in nanometers). In this figure, curves 1221 represent the upper and lower bounds of exposure deviation for cut line 1201 for various defocus levels, whereas curves 1222 represent the upper and lower bounds of exposure deviation for cut line 1202 for various defocus levels. The largest possible rectangle that fits within the overlap of these two areas defines a common process window 1223. In this embodiment, common process window 1223 indicates that the defocus can vary between approximately −150 nm and 150 nm, whereas the exposure deviation can vary between approximately −10% and 10% (all while maintaining the line CD within tolerance).

FIG. 12D plots exposure latitude (%) versus depth of focus (DOF) (in nanometers), wherein exposure latitude refers to the amount of exposure dose variation and DOF refers to the amount of focus variation. In this figure, curves 1231 represent the upper and lower bounds of exposure latitude for cut line 1201 for various DOFs, whereas curves 1232 represent the upper and lower bounds of exposure latitude for cut line 1202 for various DOFs. Note that curves 1231 and 1232 share the same lower boundary. The largest possible rectangle that fits under the common lower boundary defines a common process window 1233. In this embodiment, common process window 1233 indicates that the DOF can vary between approximately 0 nm and 300 nm, whereas the exposure latitude can vary between approximately 0% and 19% (once again, while maintaining the line CD within tolerance).

Note that the information provided by process window 1233 can be derived by process window 1223. Specifically, the DOF range is equal to the total range of defocus and the exposure latitude range is equal to the total range of exposure deviation.

Figure 13B:
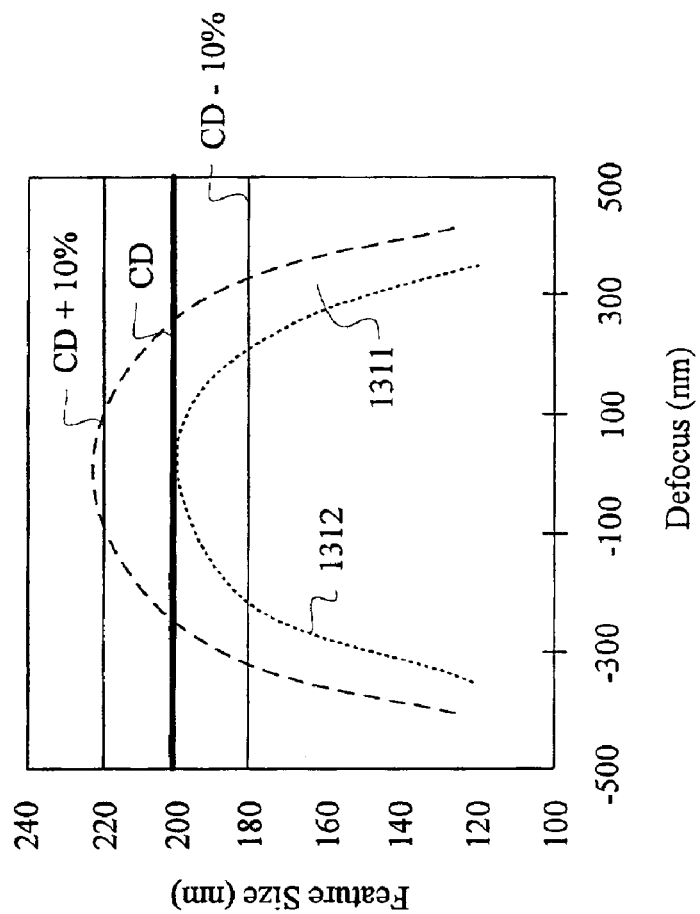
FIG. 13B illustrates a plot of feature size versus defocus for the feature of FIG. 13A.
Figure 13A:
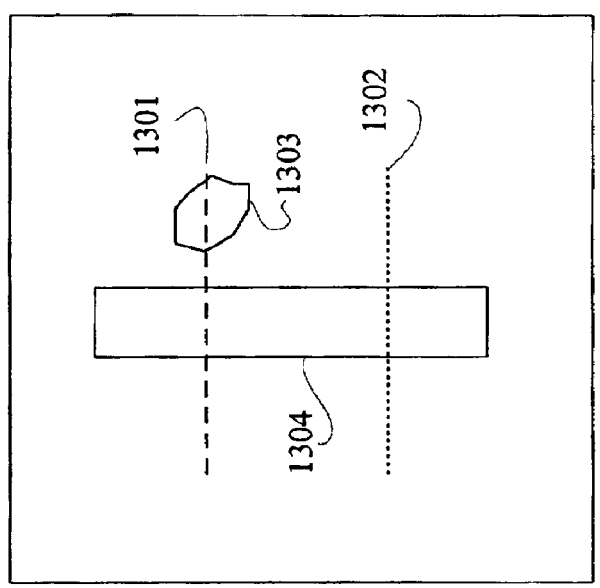
FIG. 13A illustrates a mask including a feature and a defect proximate to the feature, wherein this defect is larger than the defect of FIG. 12A.

FIG. 13A illustrates a mask having a feature 1304 and a defect 1303. Although feature 1304 is the same size as feature 1204, defect 1303 is significantly larger than defect 1203. Thus, the width of printed feature 1304 at cut line 1301 will be wider than the width of printed feature 1304 at cut line 1302. Moreover, as described in detail below, defect 1303 will significantly decrease the process window compared to defect 1203.

FIG. 13B shows a plot of feature size (also in nanometers) versus defocus (in nanometers). Once again, the bold horizontal line indicates that the target CD is 200 nm, whereas the other horizontal lines indicate a +/− 10% error of this target CD. Curves 1311 and 1312 are generated by exposing (or simulating exposure of) the mask including defect 1323 and analyzing the CDs of the printed feature at cut lines 1301 and 1302 at various defocus levels (in this case, −500 nm to 500 nm). Curves 1311 and 1312 represent the CD analysis at cut lines 1301 and 1302, respectively.

As noted previously, each feature size on curve 1312 has a corresponding larger feature size on curve 1311. For example, at −300 nm defocus, the feature size at cut line 1302 (see curve 1312) is approximately 150 nm, whereas the feature size at cut line 1301 (see curve 1311) is approximately 185 nm. Note that an acceptable defocus window for both curves, i.e. between horizontal lines CD +/− 10%, is between approximately −208 nm and −100 nm as well as between approximately 100 nm and 208 nm.

Figure 13D:
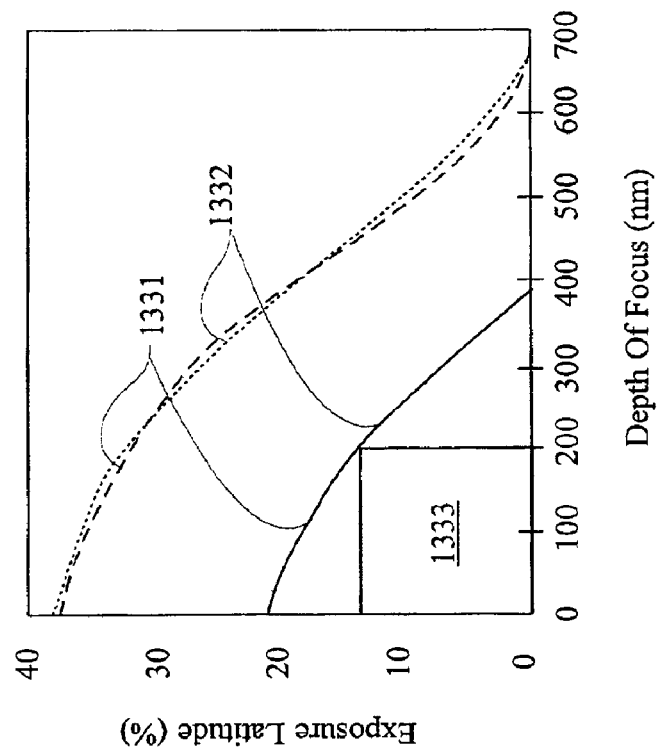
FIG. 13D illustrates a plot of exposure latitude versus depth of focus for the feature of FIG. 13A.
Figure 13C:
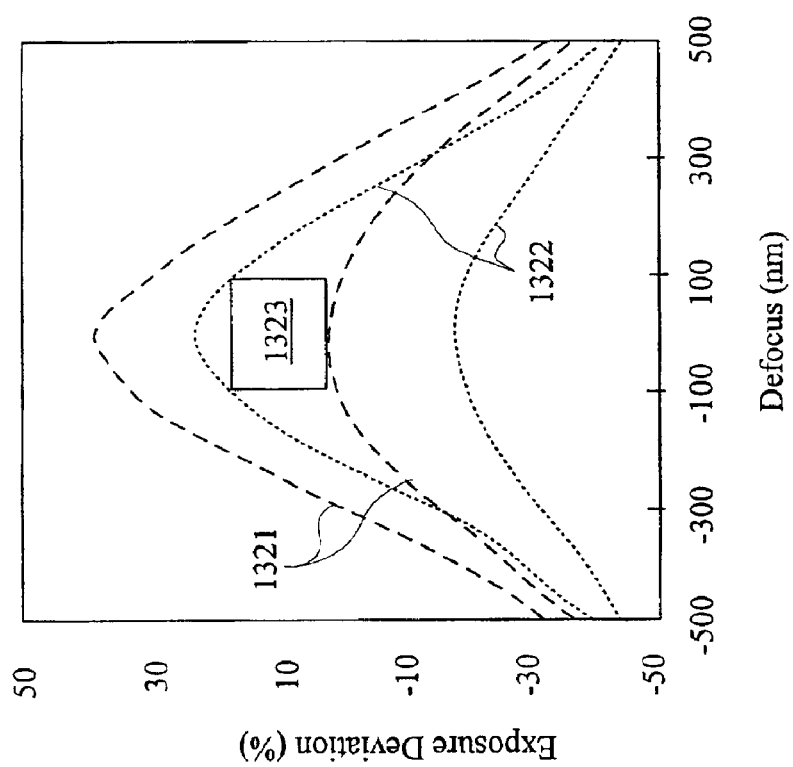
FIG. 13C illustrates a plot of exposure deviation versus defocus for the feature of FIG. 13A.

FIG. 13C illustrates a plot of percentage exposure deviation versus defocus (in nanometers). In this figure, curves 1321 represent the upper and lower bounds of exposure deviation for the CD corresponding to cut line 1301 for various defocus levels, whereas curves 1322 represent the upper and lower bounds of exposure deviation for the CD corresponding to cut line 1302 for various defocus levels. The largest possible rectangle that fits within the overlap of these two areas defines a common process window 1323. In this embodiment, common process window 1323 indicates that the defocus can vary between approximately −100 nm and 100 nm, whereas the exposure deviation can vary between approximately 2% and 15% (all while maintaining the line CD within tolerance).

FIG. 13D plots exposure latitude (%) versus DOF (in nanometers). In this figure, curves 1331 represent the upper and lower bounds of exposure latitude for the CD corresponding to cut line 1301 for various DOFs, whereas curves 1332 represent the upper and lower bounds of exposure latitude for the CD corresponding to cut line 1302 for various DOFs. Note that curves 1331 and 1332 share substantially the same upper and lower boundaries. The largest possible rectangle that fits under the common lower boundary defines a common process window 1333. In this embodiment, common process window 1333 indicates that the DOF can vary between approximately 0 nm and 200 nm, whereas the exposure latitude can vary between approximately 0% and 12% (once again, while maintaining the line CD within tolerance).

Note that process windows 1223/1233 are significantly larger than process windows 1323/1333. As seen from this example, a larger defect size reduces the process window. Therefore, various process windows can be compared to determine defect printability. Specifically, the process window for a defect-free feature could be compared to one or more process windows of features having a defect proximate to such feature(s). In a typical embodiment, the customer could set a range of acceptable deviation from the process window for the defect-free feature.

The process described above is equally applicable to defects that form part of the feature. For example, FIG. 14A illustrates a mask having a feature 1404 and an integrally formed defect 1403. Defect 1403 will affect the width of feature 1404. Specifically, the width of feature 1404 at cut line 1401 will be larger than the width at cut line 1402.

Figure 14B:
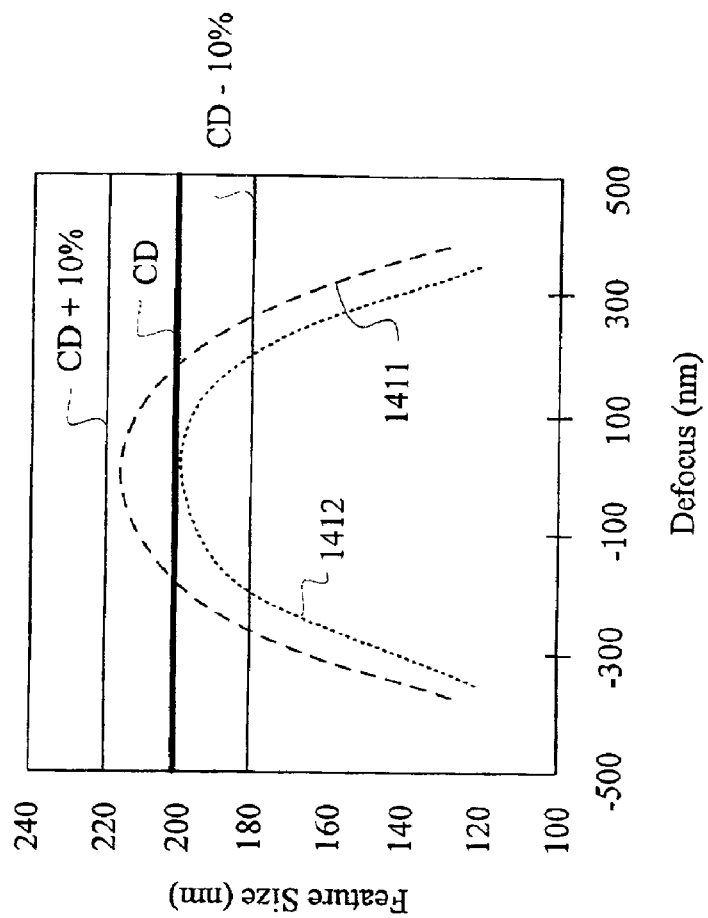
FIG. 14B illustrates a plot of feature size versus defocus for the feature of FIG. 14A.
Figure 14A:
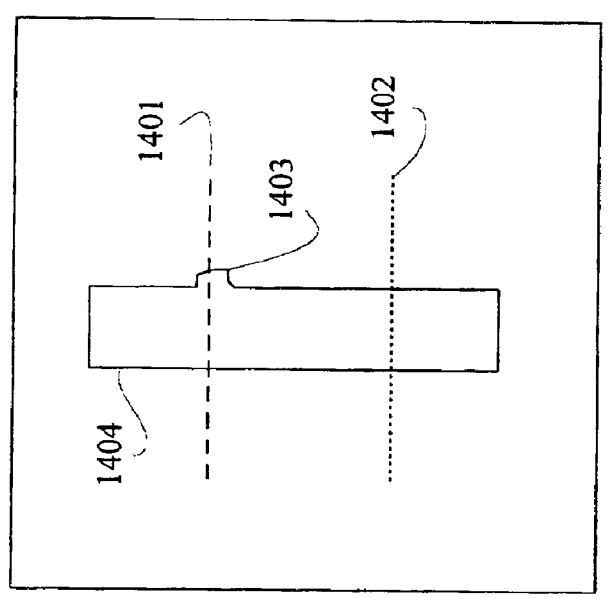
FIG. 14A illustrates a mask including a feature having a defect integrally formed therein.

FIG. 14B shows a plot of feature size (also in nanometers) versus defocus (in nanometers). In this figure, the bold horizontal line indicates that the target CD is 200 nm, whereas the other horizontal lines indicate a +/− 10% error of this target CD. Curves 1411 and 1412 are generated by exposing (or simulating exposure of) the mask including defect 1403 and analyzing the CDs of the printed feature at cut lines 1401 and 1402 at various defocus levels (in this case, −500 nm to 500 nm). Curves 1411 and 1412 represent the CD analysis at lines 1401 and 1402, respectively. In this embodiment, energy of 3.9 mJ/cm2 was assumed for development.

Logically, each feature size on curve 1412 has a corresponding larger feature size on curve 1411. For example, at −300 nm defocus, the feature size at cut line 1402 (see curve 1412) is approximately 150 nm, whereas the feature size at cut line 1401 (see curve 1411) is approximately 165 nm. Note that an acceptable defocus window for both curves, i.e. between horizontal lines CD +/− 10%, is between approximately −208 nm and 208 nm.

Figure 14D:
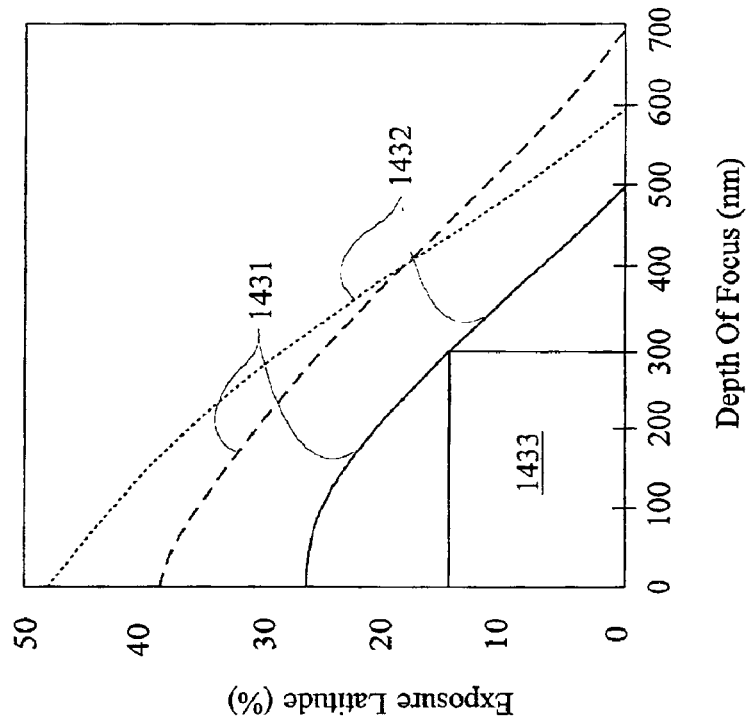
FIG. 14D illustrates a plot of exposure latitude versus depth of focus for the feature of FIG. 14A.
Figure 14C:
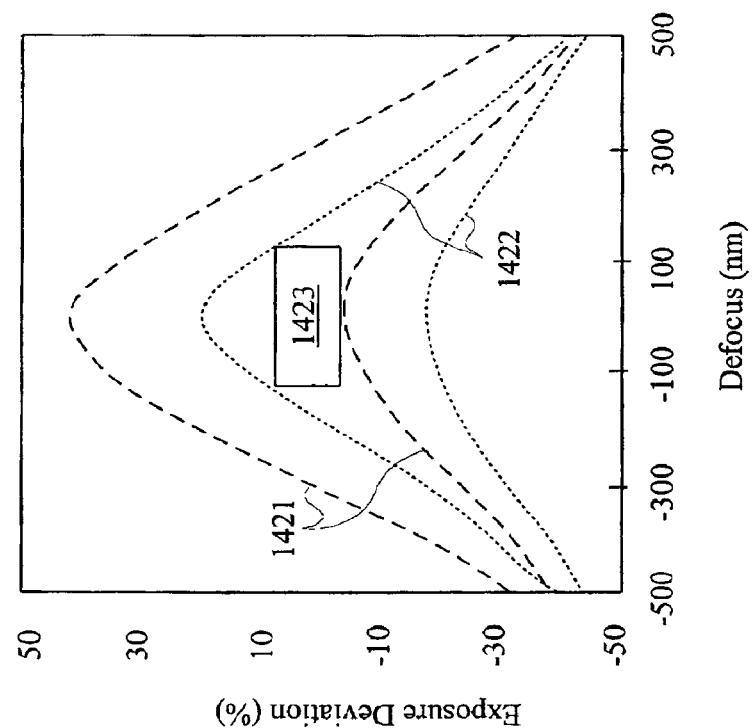
FIG. 14C illustrates a plot of exposure deviation versus defocus for the feature of FIG. 14A.

FIG. 14C illustrates a plot of percentage exposure deviation versus defocus (in nanometers). In this figure, curves 1421 represent the upper and lower bounds of exposure deviation for cut line 1401 for various defocus levels, whereas curves 1422 represent the upper and lower bounds of exposure deviation for cut line 1402 for various defocus levels. The largest possible rectangle that fits within the overlap of these two areas defines a common process window 1423. In this embodiment, common process window 1423 indicates that the defocus can vary between approximately −150 nm and 150 nm, whereas the exposure deviation can vary between approximately −5% and 9% (all while maintaining the line CD within tolerance).

FIG. 14D plots exposure latitude (%) versus DOF (in nanometers). In this figure, curves 1431 represent the upper and lower bounds of exposure latitude for cut line 1401 for various DOFs, whereas curves 1432 represent the upper and lower bounds of exposure latitude for cut line 1402 for various DOFs. Note that curves 1431 and 1432 share the same lower boundary. The largest possible rectangle that fits under the common lower boundary defines a common process window 1433. In this embodiment, common process window 1433 indicates that the DOF can vary between approximately 0 nm and 300 nm, whereas the exposure latitude can vary between approximately 0% and 14% (once again, while maintaining the line CD within tolerance).

As noted previously, the information provided by process window 1433 can be derived by process window 1423. Specifically, the DOF range is equal to the total range of defocus and the exposure latitude range is equal to the total range of exposure deviation.

Figure 15B:
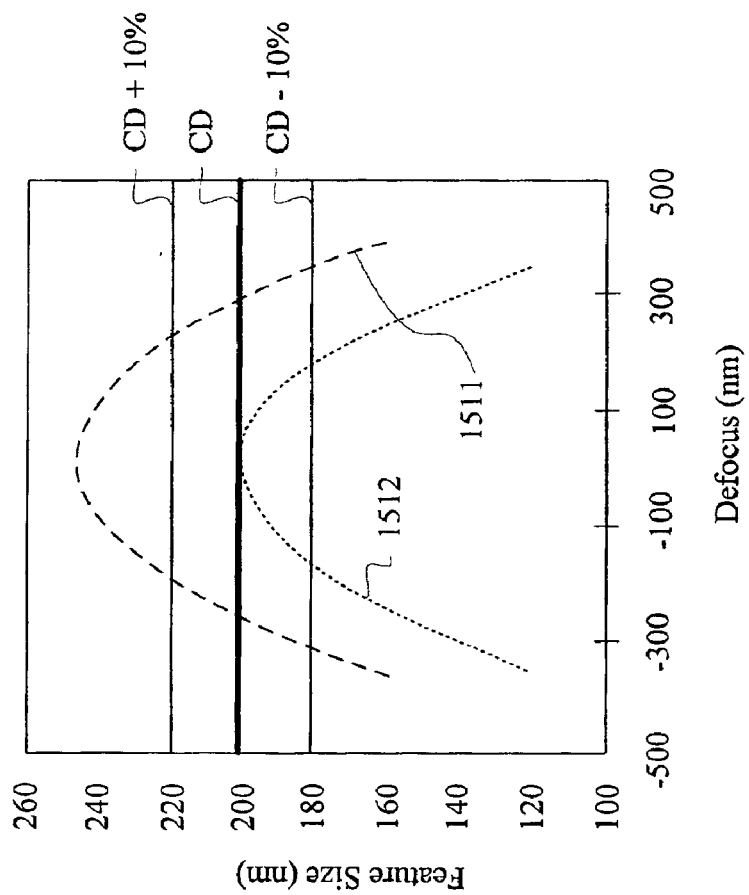
FIG. 15B illustrates a plot of feature size versus defocus for the feature of FIG. 15A.
Figure 15A:
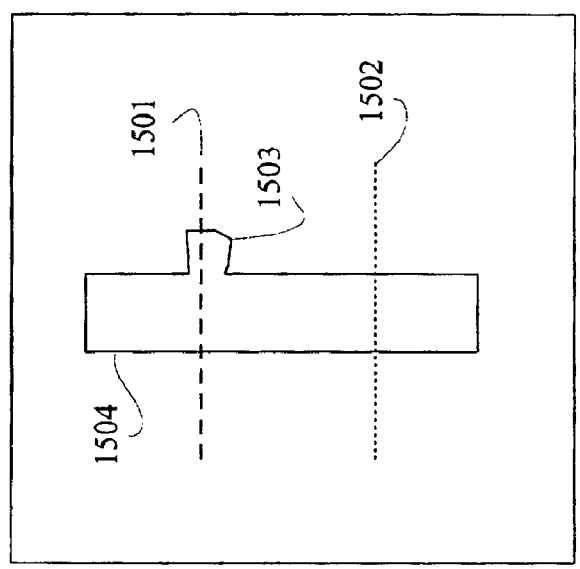
FIG. 15A illustrates a mask including a feature having a defect integrally formed therein, wherein this defect is larger than the defect of FIG. 14A.

FIG. 15A illustrates a mask having a feature 1504 and a defect 1503. Although feature 1504 is the same size as feature 1404, defect 1503 is significantly larger than defect 1403. Thus, the width of printed feature 1504 at cut line 1501 will be wider than the width of printed feature 1404 at cut line 1401. Moreover, as described in detail below, defect 1503 will significantly decrease the process window compared to defect 1403.

FIG. 15B shows a plot of feature size (also in nanometers) versus defocus (in nanometers). Once again, the bold horizontal line indicates that the target CD is 200 nm, whereas the other horizontal lines indicate a +/− 10% error of this target CD. Curves 1511 and 1512 are generated by exposing (or simulating exposure of) the mask including defect 1503 and analyzing the CDs of the printed feature at cut lines 1501 and 1502 at various defocus levels (in this case, −500 nm to 500 nm). Curves 1511 and 1512 represent the CD analysis at cut lines 1501 and 1502, respectively.

As noted previously, each feature size on curve 1512 has a corresponding larger feature size on curve 1511. For example, at −300 nm defocus, the feature size at cut line 1502 (see curve 1512) is approximately 150 nm, whereas the feature size at cut line 1501 (see curve 1511) is approximately 198 nm. Note that an acceptable defocus window for both curves, i.e. between horizontal lines CD +/− 10%, is no longer attainable.

Figure 15D:
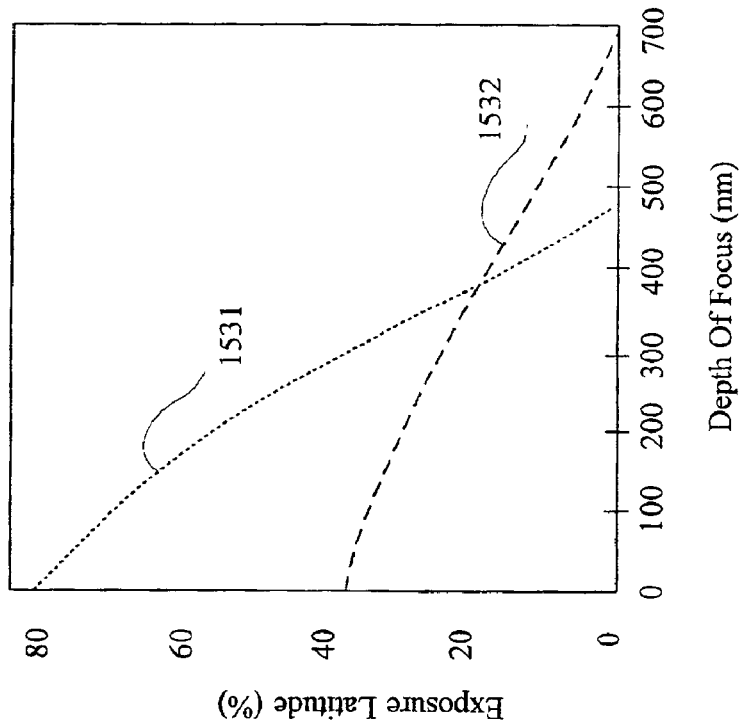
FIG. 15D illustrates a plot of exposure latitude versus depth of focus for the feature of FIG. 15A.
Figure 15C:
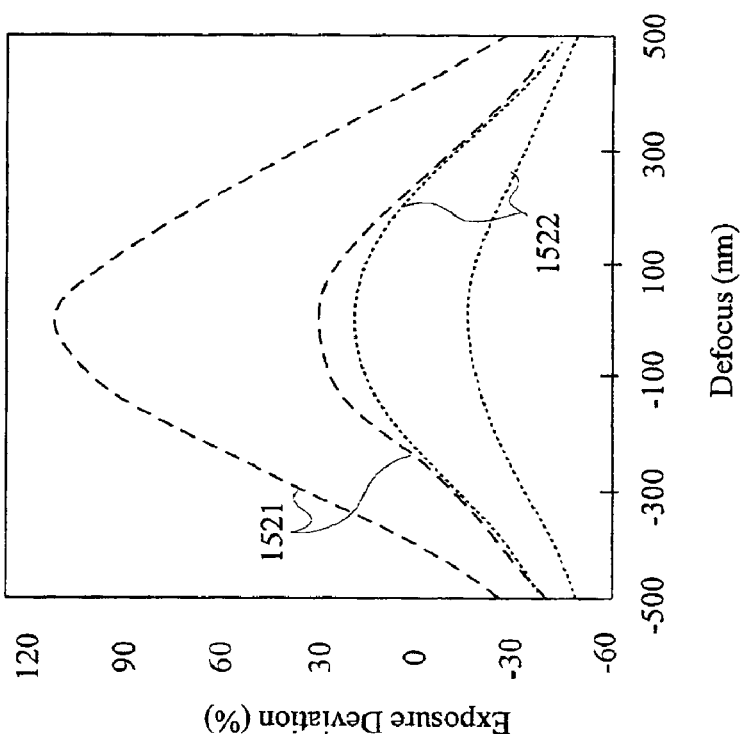
FIG. 15C illustrates a plot of exposure deviation versus defocus for the feature of FIG. 15A.

FIG. 15C illustrates a plot of percentage exposure deviation versus defocus (in nanometers). In this figure, curves 1521 represent the upper and lower bounds of exposure deviation for the CD corresponding to cut line 1501 for various defocus levels, whereas curves 1522 represent the upper and lower bounds of exposure deviation for the CD corresponding to cut line 1502 for various defocus levels. In this case, the two areas defined by curves 1521 and 1522 do not overlap. Therefore, no common process window exists. Thus, defect 1503 will effectively prevent feature 1504 from printing within tolerance.

FIG. 15D plots exposure latitude (%) versus DOF (in nanometers). In this figure, curve 1531 represents the upper bounds of exposure latitude for the CD corresponding to cut line 1501 for various DOFs, whereas curve 1532 represents the upper bounds of exposure latitude for the CD corresponding to cut line 1502 for various DOFs. Note that curves 1531 and 1532 do not share any lower boundary. Therefore, no common process window exists, thereby confirming the information derived from FIG. 15D.

In FIGS. 12–15, the use of process windows to determine defect printability has been applied to lines. However, this use of process windows is also applicable to the printability of contacts and vias. FIGS. 16A–16D respectively illustrate a defect-free contact 1601 on a mask, a plot 1602 of feature size versus defocus, a plot 1603 of exposure deviation versus defocus (and a resulting process window), and a plot 1604 of exposure latitude versus DOF (and its resulting process window).

In contrast, FIGS. 17A–17D respectively illustrate a contact 1701 on a mask, a plot 1702 of feature size versus defocus, a plot 1703 of exposure deviation versus defocus (and a resulting process window), and a plot 1704 of exposure latitude versus DOF (and its resulting process window). Note that contact 1701 has noticeably significant CD variations and thus, under prior art analysis, could be considered a moderately defective contact.

Figure 16B:
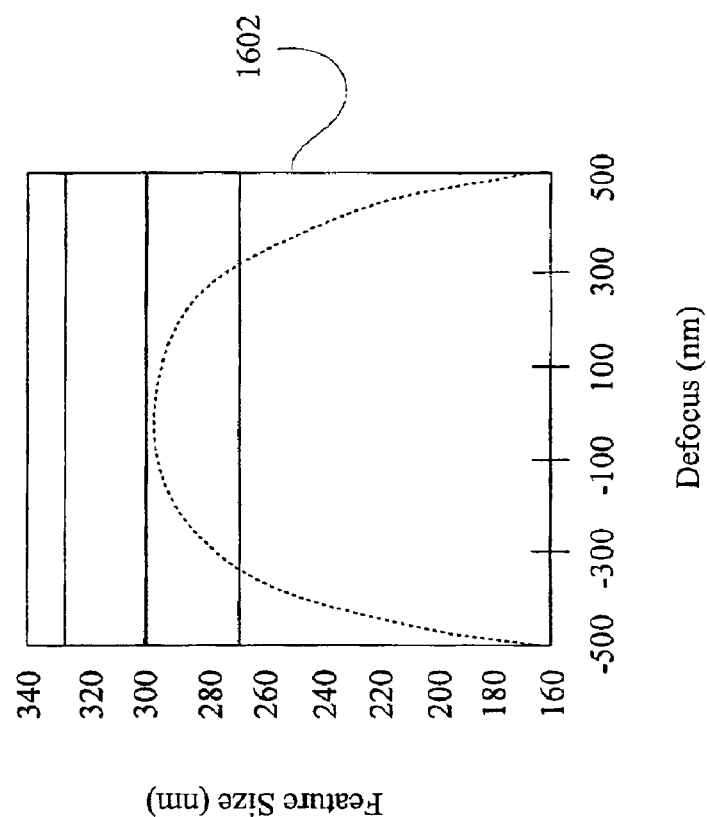
FIG. 16B illustrates a plot of feature size versus defocus for the contact of FIG. 16A.
Figure 16A:
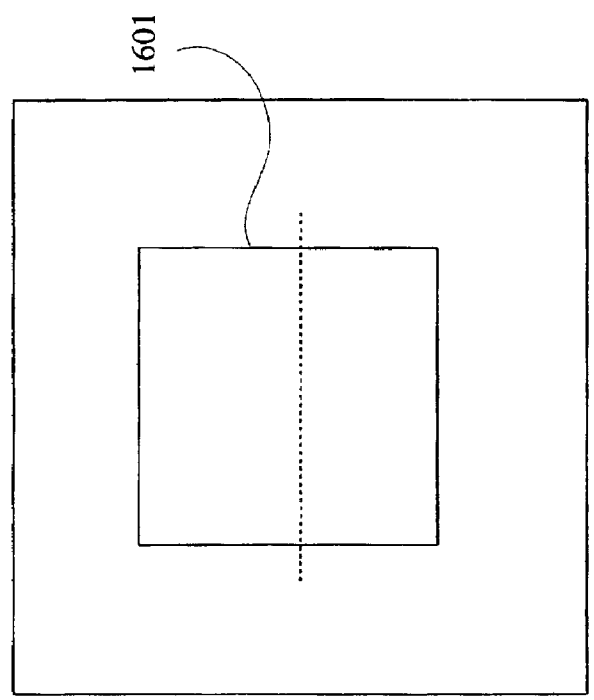
FIG. 16A illustrates a mask including a contact (or via or post).
Figure 16D:
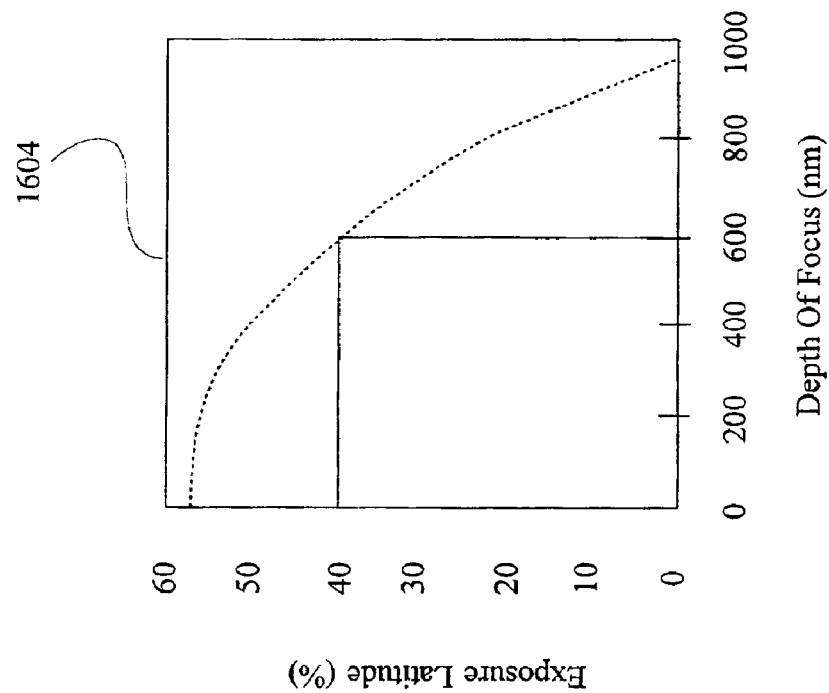
FIG. 16D illustrates a plot of exposure latitude versus depth of focus for the contact of FIG. 16A.
Figure 16C:
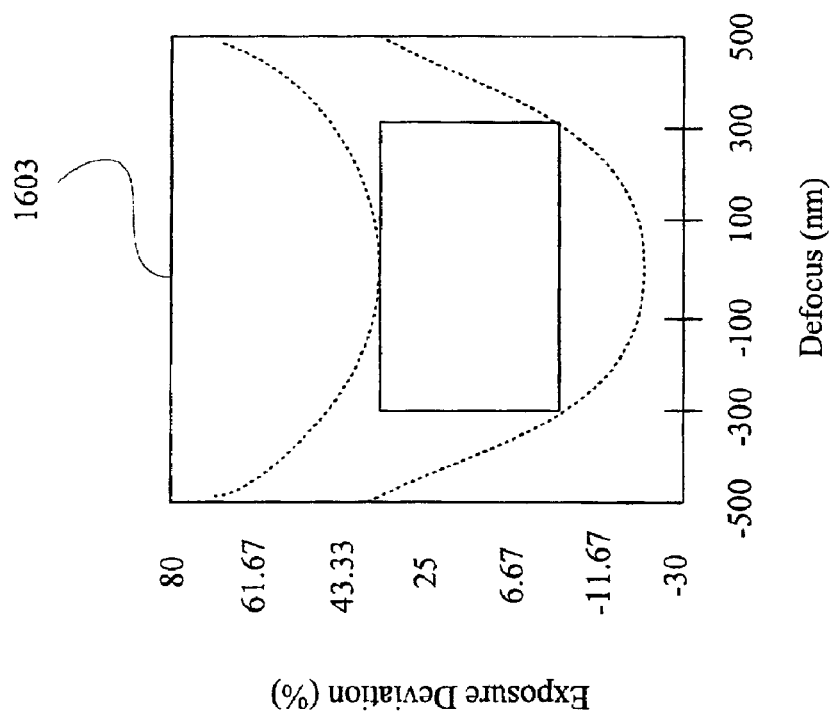
FIG. 16C illustrates a plot of exposure deviation versus defocus for the contact of FIG. 16A.
Figure 17B:
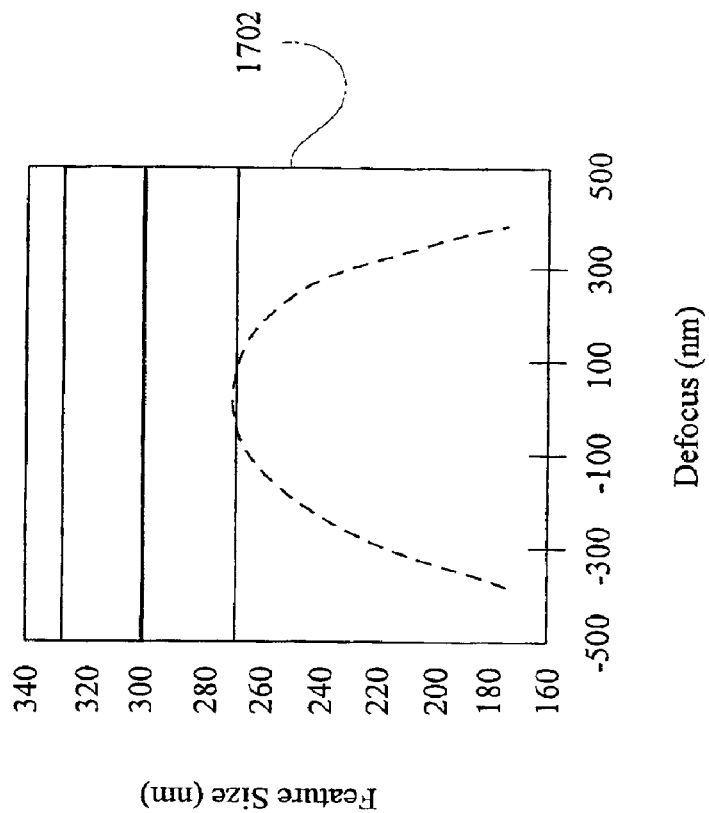
FIG. 17B illustrates a plot of feature size versus defocus for the contact of FIG. 17A.
Figure 17A:
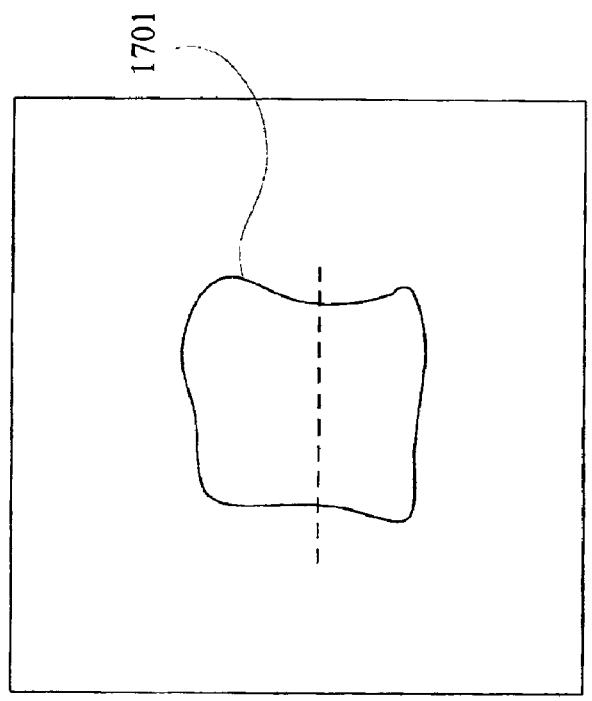
FIG. 17A illustrates a mask including a contact (or via or post) having significant critical dimension (CD) variation.
Figure 17D:
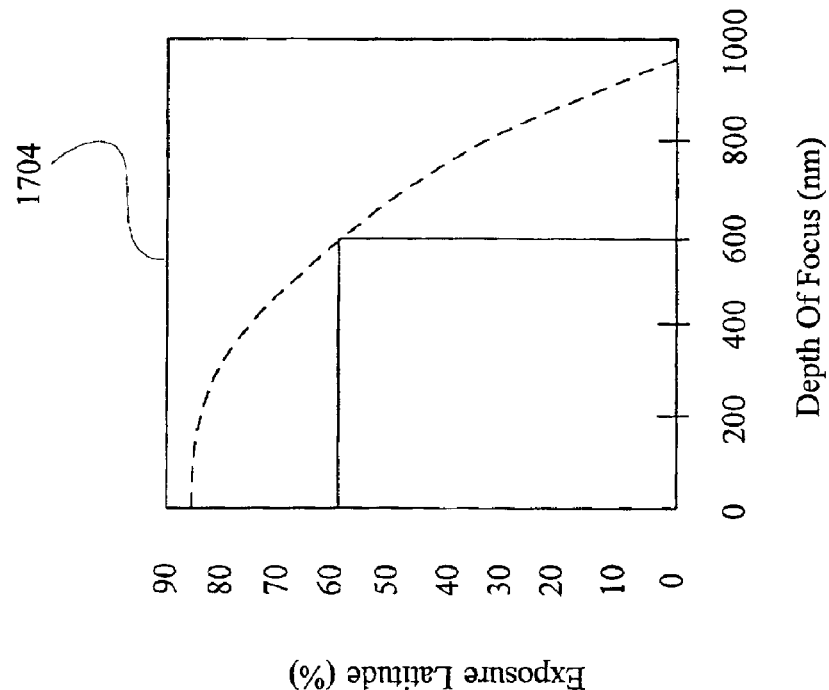
FIG. 17D illustrates a plot of exposure latitude versus depth of focus for the contact of FIG. 17A.
Figure 17C:
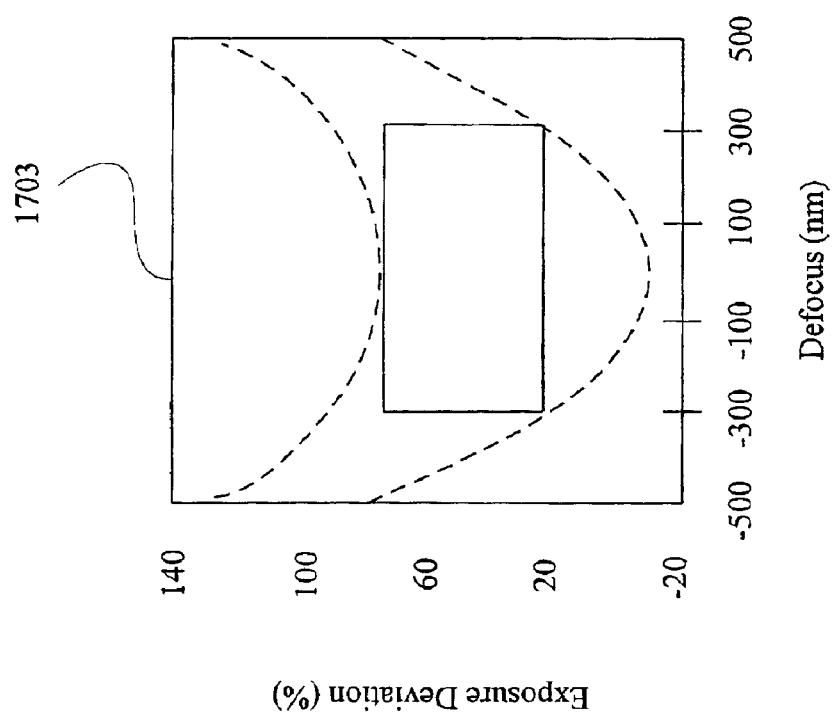
FIG. 17C illustrates a plot of exposure deviation versus defocus for the contact of FIG. 17A.

However, an analysis of the process windows of FIGS. 17C and 17D compared to the process windows of FIGS. 16C and 16D reveals that contact 1701, although exhibiting considerable CD variation, has one process window relatively similar to those of contact 1601. Specifically, referring to FIGS. 17D and 16D, contacts 1701 and 1601 both have a common depth of focus between 0 and 600 nm and a substantially similar exposure latitude, i.e. between 0 and 58% for contact 1701 and between 0 and 40% for contact 1601. However, although contacts 1701 and 1601 have the identical defocus (i.e. between −300 nm and 300 nm), these contacts have significantly different percentage exposure deviations. Specifically, contact 1701 has an exposure deviation between approximately 22% and 80%, whereas contact 1601 has an exposure deviation between approximately −3 and 37%. As a result, a common process window, albeit small, can exist for both contacts 1701 and 1601.

Thus, analyzing the process windows associated with a feature can provide an objective means of determining the printability of that feature based on a defect. For example, a defect severity can be derived from the amount of overlap between two process windows (i.e. the common process window), wherein one process window is extracted from the defect cut line and another process window is extracted from the reference cut line. Specifically, in accordance with this embodiment, defect printability analysis generator 515 could determine a common process window for the features provided in masks 501A and 501B and provide this information in impact report 516.

Repairs of the Physical Mask

Figure 18:
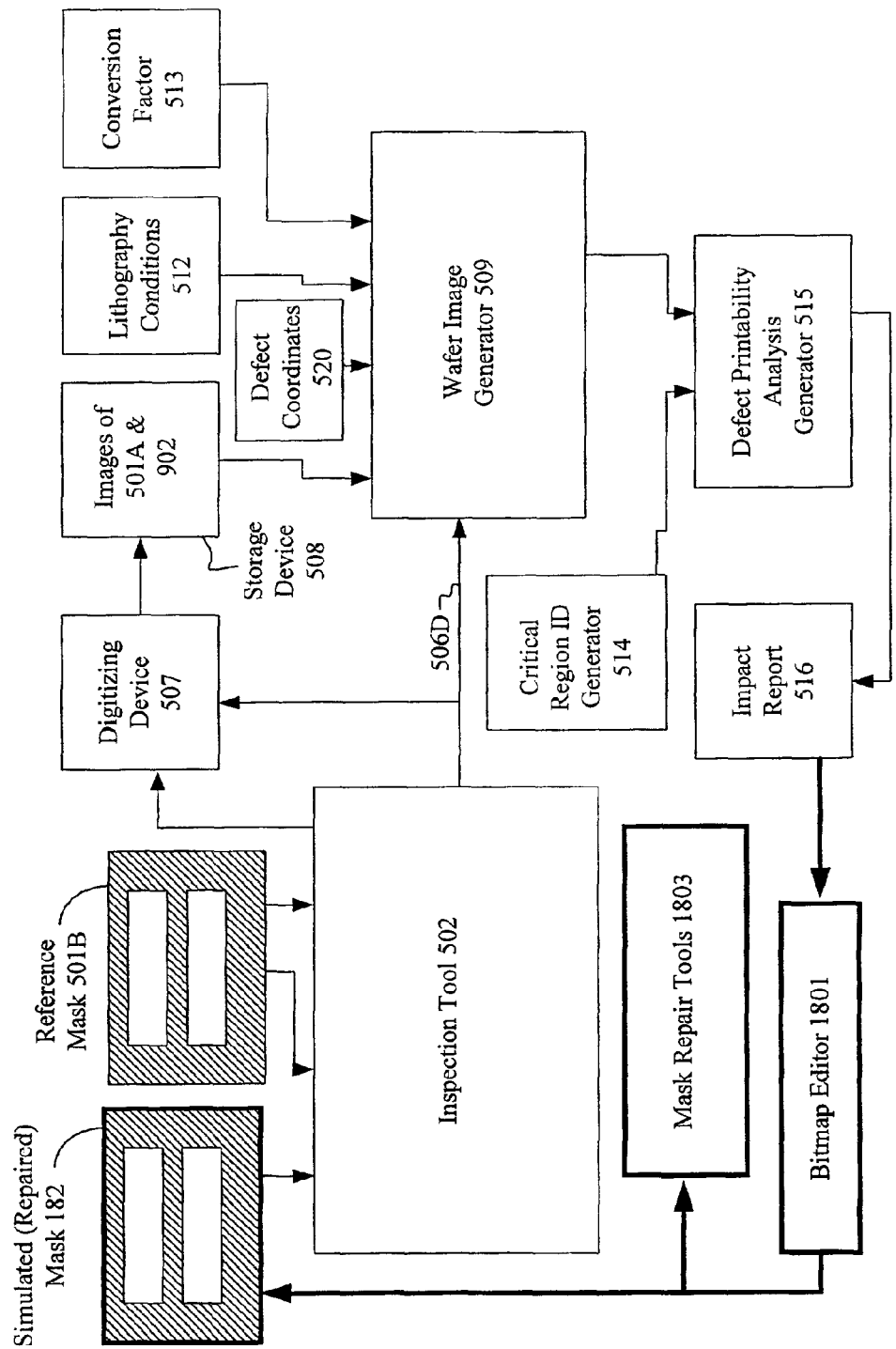
FIG. 18 illustrates a mask repair process and system.

FIG. 18 illustrates one process that can be used to analyze repairs that could be done on a physical mask. As shown in FIG. 18, using impact report 516 (or portions therein), a bitmap editor 1801 can indicate possible corrections to be made to the physical mask (for example, physical mask 501A) to eliminate or significantly minimize the effects of one or more defects. Bitmap editor 1801 can then output a simulated mask 1802 including these corrections. Thus, simulated mask 1802 is a possible, repaired version of the physical mask. Note that bitmap editor 1801 can be separate from or use the same tools as wafer image generator 509.

Simulated mask 1802 can be inspected by inspection tool 502 and used by wafer image generator 509 to generate a new, simulated wafer image (not shown) and a new impact report that indicates the success of the possible corrections provided in mask 1802. If the corrections are acceptable, then bitmap editor 1801 can provide the correction information directly to mask repair tools 1803 for repair of the physical mask. If the customer desires additional optimization or analysis of different parameters, then the above-described processes can be repeated until either the corrections are deemed to be within an acceptable range or bitmap editor 1801 indicates that the desired result cannot be attained by repairing the physical mask.

In one embodiment, bitmap editor 1801 can also indicate the optimized mask writing strategy. For example, a laser tool can be used for opaque defects (e.g. removal of chromium defects), whereas a focused ion beam tool can be used for clear defects (e.g. deposition of chromium). Note that laser and focused ion beam tools can also be used for deposition and removal, respectively. Generally, a focused ion beam tool provides more precision than a laser tool. However, the focused ion beam tool is typically slower than the laser tool. Bitmap editor 1801 can receive inputs (not shown) that indicate customer time or cost limitations, thereby allowing bitmap editor 1801 to optimize the repair process based on these customer parameters.

In yet another embodiment of the invention, bitmap editor 1801 can be used to provide information to wafer repair tools (not shown). Specifically, bitmap editor 1801 can include a program that compares the efficacy of repairing a mask versus repairing a wafer. In one embodiment, the program can convert non-optical (e.g. SEM, focused ion beam) images into optical images for further analysis.

Batch Processing

Of importance, defect printability analysis can be done on individual defects or on a plurality of defects. In one embodiment, inspection tool 502 and wafer image generator 509 can automatically provide outputs regarding all defects found on physical mask 501A. Thus, impact report 516 could include defect severity scores on all defects.

Alternatively, if desired, impact report 516 could include only defect severity scores above a certain value (above DSS of "5", for example). This tailored impact report could, in turn, be provided to bitmap editor 1801 (and subsequently to mask repair tools 1803). Therefore, a complete, automated defect detection and correction process could be provided, thereby significantly reducing the time for a mask to be analyzed and repaired (if appropriate).

OPC Considerations

Defect printability analysis can also eliminate the necessity of evaluating OPC features separately from other features. For example, assume that a defect located proximate to a scattering bar does not effect the printing of an associated isolated feature. However, this defect may optically interact with the scattering bar, thereby resulting in printing at least part of the scattering bar. As noted earlier, OPC features, such as scattering bars, are sub-resolution features and should not print.

In accordance with one embodiment, if an OPC feature prints (as determined by simulated wafer image) due to a defect, then the defect analysis (step 830) can indicate this error as CD changes are determined (step 831). Thus, by eliminating any complicated design rules regarding OPC features, this embodiment ensures a quick, reliable, and accurate method to identify defects adversely affecting OPC features.

Mask Quality Issues

In addition to CD changes, other printability factors, such as line edge roughness, also should factor into mask quality. However, line edge roughness of a feature on a mask is currently not measured in a meaningful way.

Figure 19B:
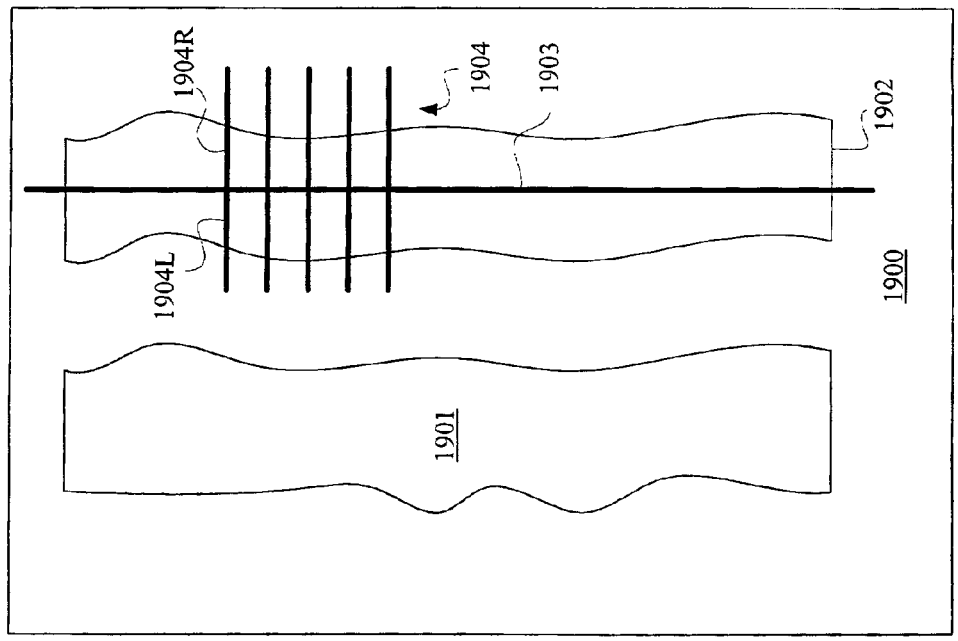
FIG. 19B illustrates a simplified layout in which line edge roughness is determined.
Figure 19A:
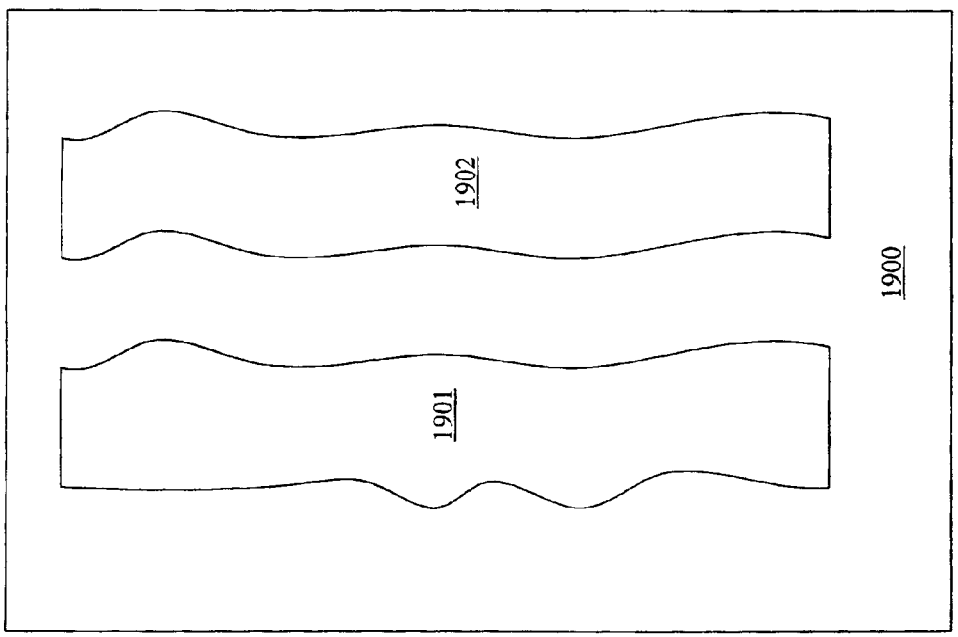
FIG. 19A illustrates a simplified layout showing a line with line edge roughness that might not exhibit critical dimension variations.

FIG. 19A illustrates a simplified, simulated wafer image 1900 including two lines 1901 and 1902. Of interest, a line with line edge roughness might not necessarily exhibit CD variations. For example, because line 1902 has substantially symmetrical line edge roughness, line 1902 might not have significant CD variations. However, both lines 1901 and 1902 should be characterized as exhibiting line edge roughness.

Referring to FIG. 19B, edges of a simulated line can be analyzed separately, thereby allowing line edge roughness to be accurately measured. Specifically, using line 1902 as an example, a centerline 1903 of line 1902 can be determined based on reference mask 501B (FIG. 5). Then, a plurality of theoretical cuts are made to line 1902 (indicated by lines 1904). Each line 1904 includes two "ribs" that extend from the centerline to opposite edges of the line. For example, rib 1904R extends from centerline 1903 to the right edge of line 1902, whereas rib 1904L extends from centerline 1903 to the left edge of line 1902. Note that ribs 1904R and 1904L when added equal the CD of line 1902.

As one feature of the invention, the lengths of the ribs on each side of centerline 1903 can be measured independently. In this manner, line edge roughness can be accurately determined for each edge of line 1902. In one embodiment, defect printability analysis generator 515 can calculate the DSS of the LER by using the equations explained in detail in reference to FIGS. 8A–8C, but modifying those equations to substitute rib length for a CD. Because all lines unavoidably have some LER, defect printability analysis generator 515 could include a look-up table indicating a threshold value for the LER. If unacceptable line edge roughness (LER) is detected, defect printability analysis generator 515 could indicate the LER of line 1902 as a "defect" listed in impact report 516. Thus, the LER could be repaired in a manner similar to that described above in reference to FIG. 18.

Advantageously, the method of using a centerline and ribs can be applied to other features on a mask. For example, even the most perfect contact on a mask can print as a circle or near circle on the wafer because of diffraction. Using high power electron beam (e-beam) lithography for printing the contact on the wafer minimizes this diffraction. However, e-beam lithography is significantly more expensive and slower than the industry-standard laser raster scan. Unfortunately, using the raster scan results in corner rounding of many, but not necessarily all, the contacts on the layout. Such corner rounding can be efficiently detected, as described in detail below.

Figures 20A, 20B:
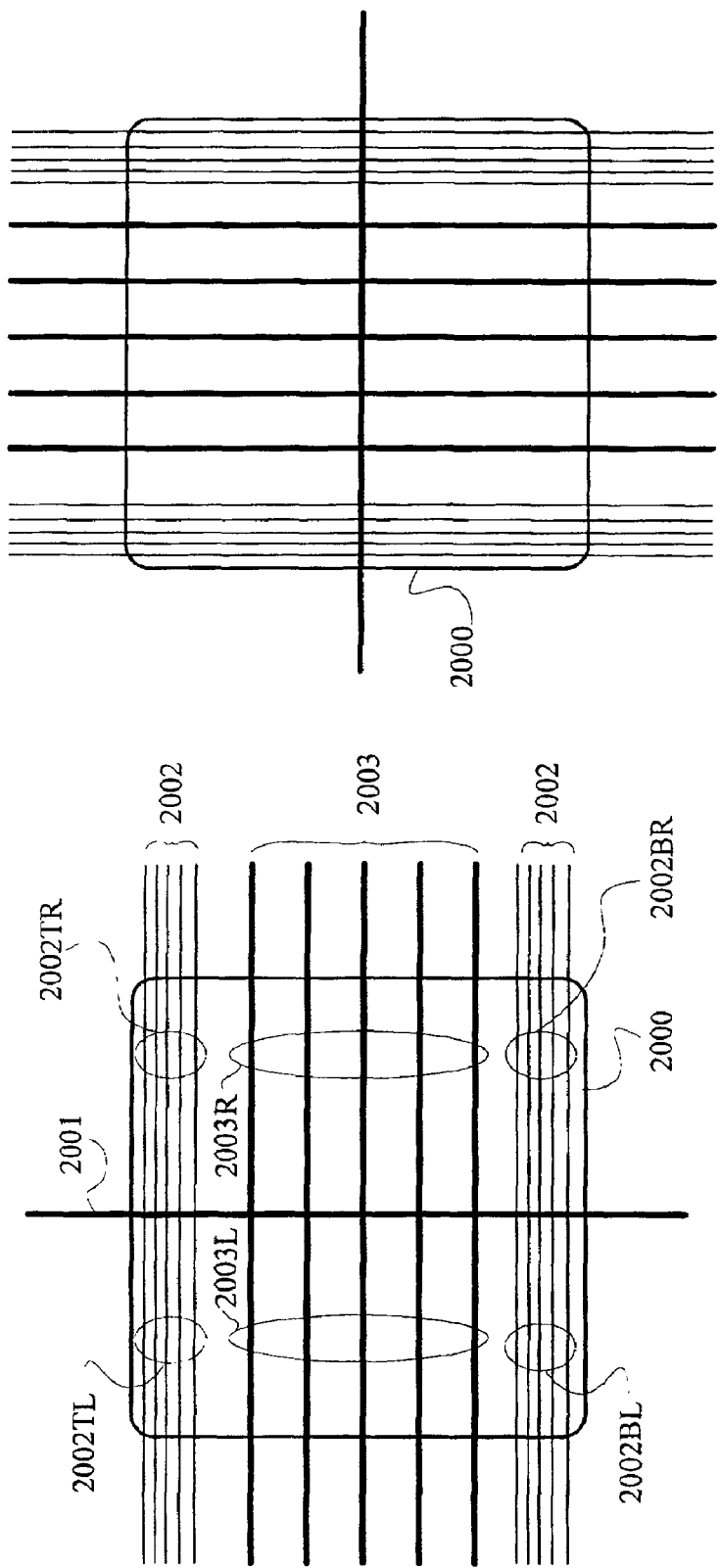
FIGS. 20A and 20B illustrate a simplified layout in which corner rounding and/or symmetry is determined.

FIG. 20A illustrates a contact 2000 having a centerline 2001, lines 2002 including ribs 2002TR (top right), 2002BR (bottom right), 2002TL (top left), and 2002BL (bottom left), and lines 2003 including ribs 2003R (right) and 2003L (left). In accordance with one feature of the invention, a plurality of theoretical, horizontal cuts made to contact 2000 can be spaced unequally, thereby providing more data points for particular elements of a feature.

In this example, corner rounding of contacts is of particular interest. Therefore, the spacing of the cuts is modified to ensure a sufficient number of data points to analyze particularly in the corners of the contact. Thus, in FIG. 20A, lines 2002 have a closer spacing than lines 2003. Corner rounding for contact 2000 can be determined by comparing the lengths of ribs 2003L to the lengths of ribs 2002TL for the top left corner and to the lengths of ribs 2002 BL for the bottom left corner. In a similar manner, the lengths of ribs 2003R can be compared to the lengths of ribs 2002TR for the top right corner and to the lengths of ribs 2003BR for the bottom right corner. Note that there are several known methods of estimating corner rounding effects (e.g. missing area, normal distance histogramming, etc.)

In some cases, performance issues relating to contacts can include whether a symmetrical contact shape is consistently made on the wafer. Advantageously, in addition to line edge roughness, the symmetry of the contact can also be determined. For example, the lengths of ribs 2002TL, 2003L, and 2002BL can be compared to the lengths of ribs 2002TR, 2003R, and 2002BR to determine the horizontal symmetry of contact 2000 from centerline 2001. The vertical symmetry of contact 2000 can be determined by using vertical cuts as shown in FIG. 20B and following a similar process of rib comparison. The overall symmetry of contact 2000 (i.e. the "squareness") can be determined by comparing selected combined horizontal ribs (for example, the added lengths of one of ribs 2002TL and one of ribs 2002TR, i.e. the CD) to selected combined vertical ribs.

In one embodiment, defect printability analysis generator 515 can calculate the DSS of the symmetry by using the equations explained in detail in reference to FIGS. 8A–8C, but modifying those equations to substitute rib length for a CD. Because all contacts unavoidably have some non-symmetry, defect printability analysis generator 515 could include a look-up table indicating a threshold value for the non-symmetry. If unacceptable symmetry is detected, defect printability analysis generator 515 could indicate the contact/via as a "defect" listed in impact report 516. Thus, the symmetry could be repaired in a manner similar to that described above in reference to FIG. 18.

Note that some structures on the layout, such as hammer-heads and serifs (outer and inner corner), are provided to facilitate the accurate transferring of lines on the mask to the wafer. These structures, although not printing independently from the lines, can affect CD variations of those lines on the wafer. Thus, any variations of these structures due to printing the mask can also adversely affect the printing of the lines associated with those structures on the wafer. By examining the CD variations or corner rounding of the lines having associated structures, the quality of these structures can also effectively be analyzed.

Other Embodiments

Defect printability analysis, defect severity score, and mask quality assessment are described above in various embodiments. Variations and modifications to those embodiments will be apparent to those skilled in the art. For example, as described above, a physical mask and a corresponding, defect-free reference image are inspected. In one embodiment described above, the defect-free reference image is a simulated image of the layout of the physical mask. In an alternative embodiment, the defect-free reference image is a defect-free area of the physical mask having the same pattern. In yet another embodiment, the defect-free reference image is a simulated image of the mask as it is processed in manufacturing. In yet another embodiment, the defect-free reference image is a physical mask image as compensated for with microscope (lens) effects.

Figure 1:
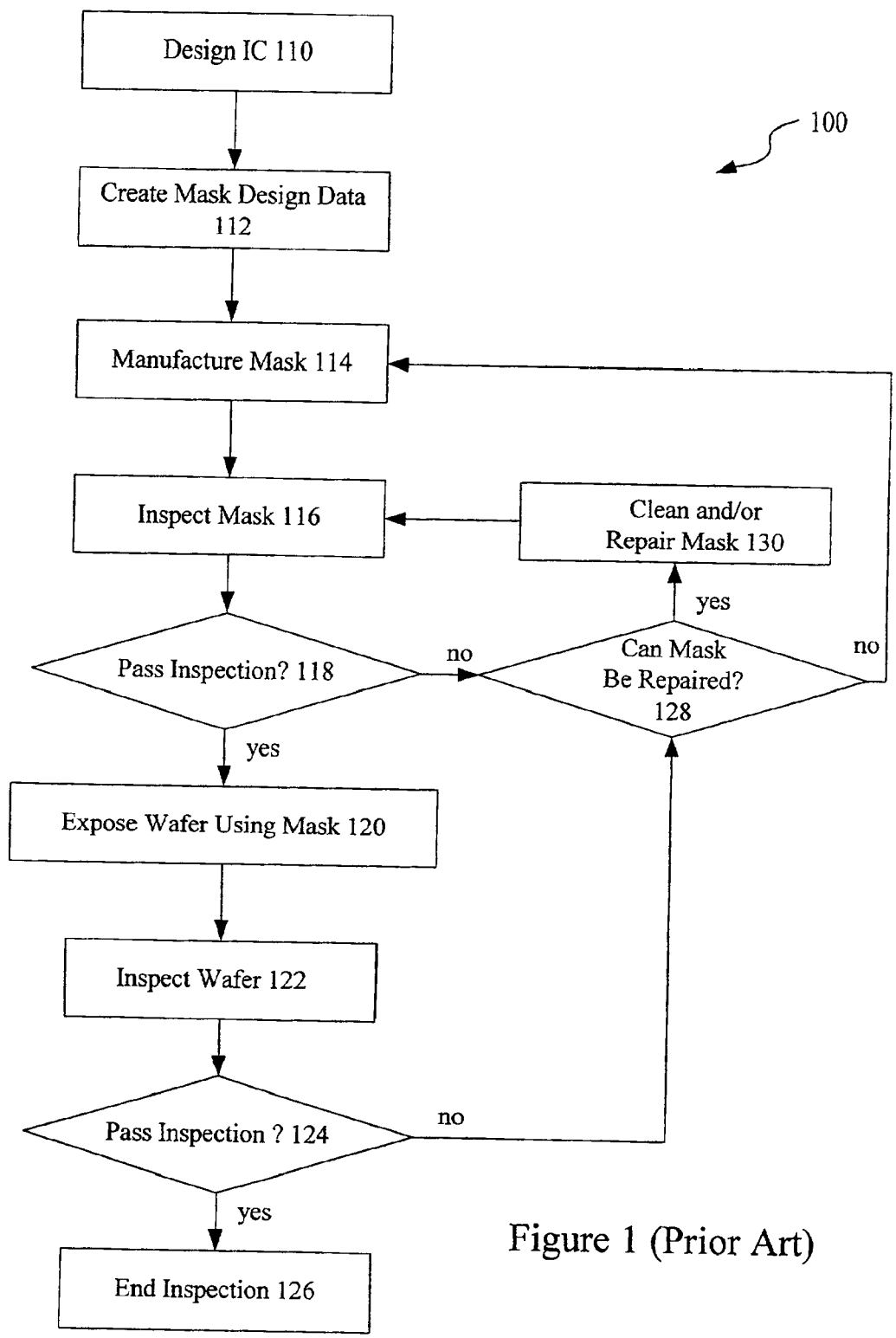
FIG. 1 illustrates a prior art mask inspection process.
Figure 2:
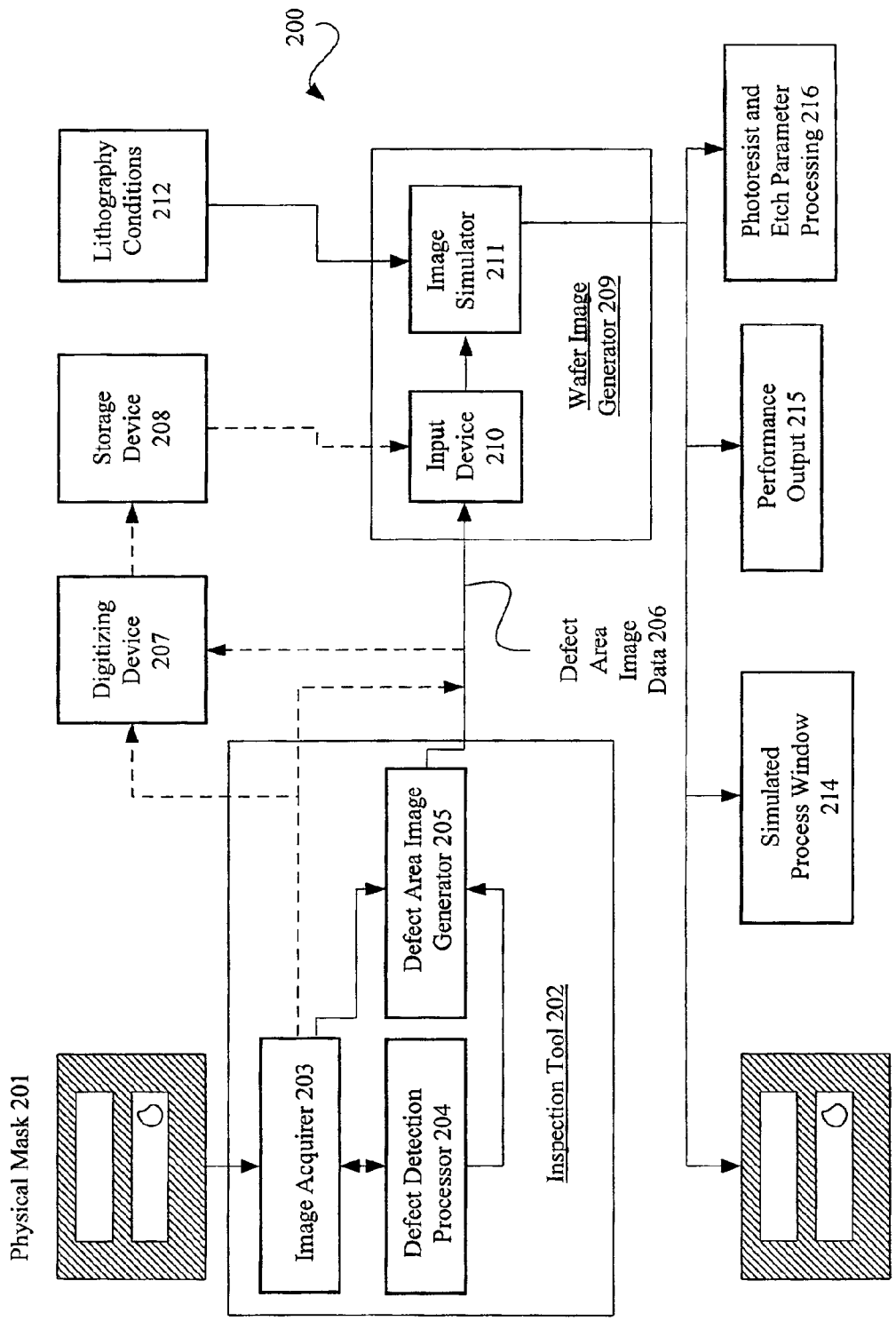
FIG. 2 illustrates a known mask inspection process and system developed by Numerical Technologies, Inc.

In a standard mask fabrication process, such as that shown in FIG. 1, the defect printability/mask quality analysis described above can be included in mask inspection step 116. Additionally, the mask quality analysis described above is equally applicable to wafer repair processes. For example, after the wafer fails inspection as determined in step 124, rather than proceeding to mask repair steps 128 and 130, process steps for repairing the wafer could be added. In yet another embodiment, in addition to the defect severity score, impact report 516 (FIG. 5) could include other performance output, such as cross-section contour lines, light intensity data, critical dimensions at different defocuses, and phase transmission data including effect on critical dimensions. Therefore, the present invention is limited only by the attached claims.

What is claimed is:

1. A method for determining edge roughness of a feature in a mask, the method comprising:
   determining a centerline of the feature based on a representation of the mask;
   measuring a first length of a first rib extending from the centerline to one edge of the feature;
   measuring a second length of a second rib extending from the centerline to the one edge of the feature; and
   comparing the first and second lengths to determine the edge roughness.

2. The method of claim 1, wherein the representation includes a layout of the mask.

3. The method of claim 1, wherein the representation includes a layout of one layer of an integrated circuit.

4. The method of claim 1, wherein the feature is a line.

5. The method of claim 1, wherein the feature is a contact.

6. A method of repairing a mask, the method comprising:
   determining an edge roughness of a feature on the mask, wherein if the edge roughness is outside a predetermined value, then using a lithography tool to repair the mask, wherein determining the edge roughness includes determining a centerline of the feature based on a defect-free representation of the feature.

7. The method of claim 6, wherein the predetermined value is selected by a user.

8. The method of claim 6, wherein the feature includes at least one of a line and a contact.

9. A method of repairing a wafer, the method comprising:
   determining an edge roughness of a feature on the wafer, wherein if the edge roughness is outside a predetermined value, then using a lithography tool to repair the wafer, wherein determining the edge roughness includes determining a centerline of the feature based on a defect-free representation of the feature.

10. The method of claim 9, wherein the predetermined value is selected by a user.

11. The method of claim 9, wherein the feature includes at least one of a line and a contact.

12. A method of determining corner rounding of a contact in a lithographic mask, the method comprising:
    determining a centerline of the contact in a first direction;
    providing a plurality of theoretical cuts through the contact in a second direction substantially perpendicular to the first direction, wherein each cut provides a rib extending from the centerline to an edge of the contact; and
    comparing at least two ribs to determine corner rounding, one rib being located near a corner of the contact and another rib not being located near the corner.

13. A method of determining the symmetry of a contact in a lithographic mask, the method comprising:
    determining a first centerline of the contact in a first direction;
    providing a plurality of theoretical cuts through the contact in a second direction substantially perpendicular to the first direction, wherein each cut provides a first critical dimension extending from a first edge of the contact to a second edge of the contact;
    determining a centerline of the contact in the second direction;
    providing a plurality of theoretical cuts through the contact in a first direction substantially perpendicular to the first direction, wherein each cut provides a second critical dimension extending from a third edge of the contact to a fourth edge of the contact; and comparing the first and second critical dimensions to determine the symmetry of the contact.

14. A method of repairing a mask, the method comprising: determining an corner rounding of a contact on the wafer, wherein if the corner rounding is outside a predetermined value, then using a lithography tool to repair the wafer, wherein determining the corner rounding includes determining a centerline of the feature based on a defect-free representation of the feature.

15. The method of claim 14, wherein the predetermined value is selected by a user.

16. An integrated circuit comprising:
a plurality of features for performing a function; and
at least one repaired feature, wherein the at least one repaired feature resulted from an automatic defect severity score, and wherein the automatic defect severity score is based on a measurement associated with a centerline of a defect-free representation of the repaired feature.

17. The integrated circuit of claim 16, wherein the at least one repaired feature includes a line.

18. The integrated circuit of claim 16, wherein the at least one repaired feature includes a contact.

19. The integrated circuit of claim 16, wherein the at least one repaired feature includes an OPC feature.

20. The integrated circuit of claim 16, wherein the at least one repaired feature includes one of a hammerhead, a serif, and a bias.

21. A mask inspection system, the system comprising:
means for generating a simulated wafer image of a feature on a mask;
means for determining a centerline for the simulated wafer image based on a defect-free representation of the feature; and
means for measuring an aspect of the simulated wafer image based on the centerline.

22. The system of claim 21, wherein the aspect includes line edge roughness.

23. The system of claim 22, further including means for evaluating possible repairs made to the mask based on the line edge roughness.

24. The system of claim 23, further including a mask repair tool receiving signals from the means for evaluating possible repairs.

25. The system of claim 22, wherein the aspect includes corner rounding.

26. The system of claim 25, further including means for evaluating possible repairs made to the mask based on the corner rounding.

27. The system of claim 26, further including a mask repair tool receiving signals from the means for evaluating possible repairs.

28. An inspection system for analyzing a feature on a mask, the system comprising:
means for generating a simulated wafer image of the feature;
means for determining a centerline for the simulated wafer image of the feature based on a defect-free representation of the feature; and
means for determining whether the feature passes a predetermined standard.

29. The system of claim 28, wherein the predetermined standard includes line edge roughness of the simulated wafer image.

30. The system of claim 29, further including means for evaluating possible repairs made to the mask based on the line edge roughness.

31. The system of claim 30, further including a mask repair tool receiving signals from the means for evaluating possible repairs.

32. The system of claim 28, wherein the predetermined standard includes symmetry of the simulated wafer image.

33. The system of claim 32, wherein the symmetry indicates corner rounding of the simulated wafer image.

34. The system of claim 33, further including means for evaluating possible repairs made to the mask based on the corner rounding of the simulated wafer image.

35. The system of claim 34, further including a mask repair tool receiving signals from the means for evaluating possible repairs.

36. A method of quantifying a quality of a feature on a mask, the method comprising:
(a) determining a centerline of the feature;
(b) measuring a first length of a first rib extending from the centerline to one edge of the feature;
(c) measuring a second length of a second rib extending from the centerline to the one edge of the feature;
(d) comparing the first and second lengths;
(e) continuing steps (b), (c), and (d) for a plurality of times; and
(f) calculating a score for the quality of the feature based on steps (a)–(e).

37. A physical mask comprising:
at least one feature being modified based on analyzing a centerline of a simulated wafer image of the feature, the centerline determined by a defect-free representation of the feature; and
at least one feature being unmodified based on analyzing the centerline.

38. The mask of claim 37, wherein the defect-free representation of the feature includes a reference mask, the reference mask corresponding to a defect-free physical mask.

39. Computer software for determining edge roughness of a feature in a mask, the software comprising:
means for determining a centerline of the feature based on a representation of the mask;
means for measuring a first length of a first rib extending from the centerline to one edge of the feature;
means for measuring a second length of a second rib extending from the centerline to the one edge of the feature; and
means for comparing the first and second lengths to determine the edge roughness.

40. Computer software for determining corner rounding of a contact in a lithographic mask, the software comprising:
means for determining a centerline of the contact in a first direction;
means for providing a plurality of theoretical cuts through the contact in a second direction substantially perpendicular to the first direction, wherein each cut provides a rib extending from the centerline to an edge of the contact; and
means for comparing at least two ribs to determine corner rounding, one rib being located near a corner of the contact and another rib not being located near the corner.

41. Computer software for determining the symmetry of a contact in a lithographic mask, the software comprising:

means for determining a first centerline of the contact in a first direction;

means for providing a plurality of theoretical cuts through the contact in a second direction substantially perpendicular to the first direction, wherein each cut provides a first critical dimension extending from a first edge of the contact to a second edge of the contact;

means for determining a centerline of the contact in the second direction;

means for providing a plurality of theoretical cuts through the contact in a first direction substantially perpendicular to the first direction, wherein each cut provides a second critical dimension extending from a third edge of the contact to a fourth edge of the contact; and means for comparing the first and second critical dimensions to determine the symmetry of the contact.

* * * * *

UNITED STATES PATENT AND TRADEMARK OFFICE
CERTIFICATE OF CORRECTION

PATENT NO. : 6,925,202 B2
DATED : August 2, 2005
INVENTOR(S) : Linard Karklin et al.

It is certified that error appears in the above-identified patent and that said Letters Patent is hereby corrected as shown below:

Column 26,
Lines 23 and 34, insert a colon after "includes" and begin a new paragraph.
Line 24, replace "feature." with -- feature;
   providing a plurality of theoretical cuts substantially perpendicular to the centerline, wherein each cut creates a rib extending from the centerline to an edge of the feature; and
   comparing at least two ribs to determine edge roughness. --.
Line 35, replace "feature." with -- feature;
   providing a plurality of theoretical cuts substantially perpendicular to the centerline, wherein each cut creates a rib extending from the centerline to an edge of the feature; and
   comparing at least two ribs to determine edge roughness. --.

Column 27,
Line 4, replace "an" with -- any --.
Line 8, insert a colon after "includes" and begin a new paragraph; replace "feature" with -- contact --.
Line 9, replace "feature." with -- contact;
   providing a plurality of theoretical cuts substantially perpendicular to the centerline, wherein each cut creates a rib extending from the centerline to an edge of the contact; and
   comparing at least two ribs to determine corner rounding. --.
Line 19, replace "feature." with -- feature, the measurement provided by making a plurality of theoretical cuts substantially perpendicular to the centerline, each cut creating a rib extending from the centerline to an edge associated with the repaired feature, and comparing at least two ribs. --.
Line 36, replace "centerline." with -- centerline, wherein the means for measuring includes:
   means for providing a plurality of theoretical cuts substantially perpendicular to the centerline, wherein each cut creates a rib extending from the centerline to an edge of the feature; and
   means for comparing at least two ribs. --.
Line 61, replace "standard." with -- standard, wherein the means for determining includes:
   means for providing a plurality of theoretical cuts substantially perpendicular to the centerline, wherein each cut creates a rib extending from the centerline to an edge of the feature; and
   means for comparing at least two ribs. --.

UNITED STATES PATENT AND TRADEMARK OFFICE
CERTIFICATE OF CORRECTION

PATENT NO.   : 6,925,202 B2
DATED        : August 2, 2005
INVENTOR(S)  : Linard Karklin et al.

It is certified that error appears in the above-identified patent and that said Letters Patent is hereby corrected as shown below:

<u>Column 28,</u>
Line 35, replace "centerline." with -- centerline,
   wherein the analyzing includes making a plurality of
theoretical cuts substantially perpendicular to the centerline,
each cut creating a rib extending from the centerline to an
edge of the feature, and comparing at least two ribs. --.

Signed and Sealed this

Fourteenth Day of March, 2006

JON W. DUDAS
*Director of the United States Patent and Trademark Office*